US008642513B2

(12) United States Patent
Throsby et al.

(10) Patent No.: US 8,642,513 B2
(45) Date of Patent: Feb. 4, 2014

(54) METHOD FOR PREPARING IMMUNOGLOBULIN LIBRARIES

(75) Inventors: Mark Throsby, Utrecht (NL); Cornelis Adriaan De Kruif, De Bilt (NL); Adrianus Quirinus Bakker, Abbekerk (NL)

(73) Assignee: Crucell Holland B.V., Leiden (NL)

( * ) Notice: Subject to any disclaimer, the term of this patent is extended or adjusted under 35 U.S.C. 154(b) by 800 days.

(21) Appl. No.: 11/990,974

(22) PCT Filed: Sep. 14, 2006

(86) PCT No.: PCT/EP2006/066355
§ 371 (c)(1),
(2), (4) Date: Feb. 21, 2008

(87) PCT Pub. No.: WO2007/031550
PCT Pub. Date: Mar. 22, 2007

(65) Prior Publication Data
US 2009/0054254 A1    Feb. 26, 2009

Related U.S. Application Data

(60) Provisional application No. 60/717,685, filed on Sep. 15, 2005.

(30) Foreign Application Priority Data

Sep. 15, 2005  (EP) .................................... 05108488
Dec. 7, 2005   (EP) .................................... 05111782
Dec. 7, 2005   (EP) .................................... 05111783

(51) Int. Cl.
*C07K 16/00*     (2006.01)
(52) U.S. Cl.
USPC ......... 506/9; 506/14; 506/16; 506/17; 506/18
(58) Field of Classification Search
None
See application file for complete search history.

(56) References Cited

U.S. PATENT DOCUMENTS

| 5,565,332 A * | 10/1996 | Hoogenboom et al. ...... 435/69.1 |
| 6,265,150 B1 | 7/2001 | Terstappen et al. |
| 7,378,276 B2 * | 5/2008 | Ettinger et al. ................ 435/377 |
| 2002/0090606 A1 | 7/2002 | Stewart et al. |
| 2003/0109042 A1 * | 6/2003 | Wu et al. ........................ 435/372 |
| 2003/0148463 A1 | 8/2003 | Kufer et al. |
| 2005/0196755 A1 * | 9/2005 | Zauderer et al. ................... 435/6 |
| 2010/0297153 A1 | 11/2010 | Geuijen et al. |
| 2010/0310572 A1 | 12/2010 | Bakker et al. |

FOREIGN PATENT DOCUMENTS

| WO | WO 98/15833 | 4/1998 |
| WO | WO 02/103012 A1 | 12/2002 |
| WO | WO 2007/031550 A2 | 3/2007 |

OTHER PUBLICATIONS

Sheets et al. PNAS 95: 6157-6162, 1998.*
Hawkins et al. Eur. J. Immunol. 22: 867-870, 1992.*
Lieby et al., 2003, Memory B cells producing somatically mutated antiphospholipid antibodies are present in healthy individuals, Hemostasis Thrombosis and Vascular Biology, 102(7): 2459-2465.*
Carsetti et al., 2004, Peripheral development of B cells in mouse and man, Immunological Reviews, 197: 179-191.*
Agematsu et al., 2000, CD27: a memory B-cell marker, Immunology Today, 21(5): 204-206.*
Klein et al., 1997, Evidence for a Large Compartment of IgM-Expressing Memory B cells in Humans, Blood, 89: 1288-1298.*
Hawkins et al., Cell selection strategies for making antibodies from variable gene libraries: trapping the memory pool, European Journal of Immunology, Mar. 1992, pp. 867-870, vol. 22, No. 3, Weinheim, Germany.
Winter et al., Man-made antibodies, Nature, Jan. 24, 1991, pp. 293-299, vol. 349, Nature Publishing Group, London, United Kingdom.
Amersdorfer et al., Genetic and immunological comparison of anti-botulinum type A antibodies from immune and non-immune human phage libraries, Vaccine, Feb. 22, 2002, pp. 1640-1648, vol. 20, No. 11-12, Butterworth Scientific, Guildford, United Kingdom.
Persson et al., Generation of diverse high-affinity human monoclonal antibodies by repertoire cloning, Proceedings of the National Academy of Sciences of USA, Mar. 15, 1991, pp. 2432-2436, vol. 88, No. 6, National Academy of Science, Washington, DC, USA.
Sheets et al., Efficient construction of a large nonimmune phage antibody library: The production of high-affinity human single-chain antibodies to protein antigens, Proceedings of the National Academy of Sciences of USA, May 26, 1998, pp. 6157-6162, vol. 95, No. 11, National Academy of Science, Washington, DC, USA.
Marks et al., Molecular evolution of proteins on filamentous phage, Mimicking the strategy of the immune system, Journal of Biological Chemistry, Aug. 15, 1992, pp. 16007-16010, vol. 267, No. 23, Birmingham, USA.
PCT International Search Report, PCT/EP2006/066355, dated Apr. 11, 2007, see note in action.
Shi et al., Functional analysis of human memory B-cell subpopulations: IgD+CD27+ B cells are crucial in secondary immune response by producing high affinity IgM, Clinical Immunology, 2003, pp. 128-137, vol. 108.
Dorsam et al., Antibodies to steroids from a small human naive IgM library, FEBS Letters, 1997, pp. 7-13, vol. 414.
Weller et al., Human blood IgM "memory" B cells are circulating splenic marginal zone B cells harboring a prediversified immunoglobulin repertoire, Blood, Dec. 1, 2004, pp. 3647-3654, vol. 104.
Dubel et al., Generation of a Human IgM Expression Library in *E. coli*, Methods in Molecular and Cellular Biology, 1992, pp. 47-52, vol. 3.
Klein et al., Human Immunoglobulin (Ig)M+IgD+ Peripheral Blood B Cells Expressing the CD27 Cell Surface Antigen Carry Somatically Mutated Variable Region Genes: CD27 as a General Marker for Somatically Mutated (Memory) B Cells, J. Exp. Med., Nov. 2, 1998, pp. 1679-1689, vol. 188, No. 9, The Rockefeller University Press.
U.S. Appl. No. 61/278,358, filed Oct. 6, 2009 Beaumont et al RSV-Specific Binding Molecule.

(Continued)

*Primary Examiner* — Cecilia J Tsang
*Assistant Examiner* — Li Lee
(74) *Attorney, Agent, or Firm* — TraskBritt

(57) ABSTRACT

The invention relates to the generation of immunoglobulin libraries and the identification and production of immunoglobulins having a specific functionality of interest.

22 Claims, 4 Drawing Sheets

(56) References Cited

OTHER PUBLICATIONS

U.S. Appl. No. 12/383,330, filed Mar. 23, 2009 Bakker et al. Agonistic Binding Molecules to the Human OX40 Receptor.

U.S. Appl. No. 12/653,779, filed Dec. 18, 2009 van den Oudenrijn et al Binding Molecules for the Treatment of Myeloid Cell Malignancies.

U.S. Appl. No. 12/589,181, filed Oct. 19, 2009 Antibody Producing Non-Human Mammals.

U.S. Appl. No. 11/990,974, filed Feb. 21, 2008 Logtenberg et al. Method for Preparing Immunoglobulin Libraries.

U.S. Appl. No. 12/590,973, filed Nov. 16, 2009 ter Meulen et al. Binding Molecules Against Sars-Coronavirus and Uses Thereof.

U.S. Appl. No. 12/227,116, filed Nov. 7, 2008 Throsby et al. Human Binding Molecules Having Killing Activity Against Enterococci and Uses Thereof.

U.S. Appl. No. 12/227,029, filed Nov. 5, 2008 Throsby et al. Human Binding Molecules Having Killing Activity Against Staphylococci and Uses Thereof.

U.S. Appl. No. 12/310,812, filed Mar. 6, 2009 van den Brink et al. Human Binding Molecules Capable of Neutralizing Influenza Virus H5N1 and Uses Thereof.

U.S. Appl. No. 12/459,661, filed Jul. 6, 2009 Bakker et al. Binding Molecules Capable of Neutralizing Rabies Virus and Uses Thereof.

U.S. Appl. No. 12/459,285, filed Jun. 29, 2009 Houtzager et al. Antibody Producing Non-Human Mammals.

U.S. Appl. No. 12/589,181, filed Oct. 19, 2009 Logtenberg et al. Antibody Producing Non-Human Mammals.

U.S. Appl. No. 11/990,974, filed Feb. 21, 2008 Throsby et al. Method for Preparing Immunoglobulin Libraries.

U.S. Appl. No. 61/215,890, filed May 11, 2009 Throsby et al. Human Binding Molecules Capable of Neutralizing Influenza Virus H3N2 and Uses Thereof.

Louise J. McHeyzer-Williams & Michael G. McHeyzer-Williams. 2005. *Antigen-Specific Memory B Cell Development*. Annu. Rev. Immunology 23: 487-513.

Klein et al., 1998. *Human Immunoglobulin (Ig)M+IgD+ Peripheral Blood B Cells Expressing the CD27 Cell Surface Antigen Carry Somatically Mutated Variable Region Genes: CD27 as a General Marker for Somatically Mutated (Memory) B Cells*. J. Exp. Med. 188(9): 1679-89.

Wirths et al., 2005. *ABCB1 transporter discriminates human resting naïve B cells from cycling transitional and memory B cells*, Eur. J. Immunol. 35:3433-3441.

Inaki Sanz et al.. 2008. *Phenotypic and functional heterogeneity of human memory B cells*, Seminars in Immunology 20: 67-82.

\* cited by examiner

SEQUENCE LISTING

```
<160> NUMBER OF SEQ ID NOS: 86

<210> SEQ ID NO 1
<211> LENGTH: 23
<212> TYPE: DNA
<213> ORGANISM: Artificial sequence
<220> FEATURE:
<223> OTHER INFORMATION: Primer OK1 (HuVK1B)

<400> SEQUENCE: 1
gacatccagw tgacccagtc tcc                                              23

<210> SEQ ID NO 2
<211> LENGTH: 23
<212> TYPE: DNA
<213> ORGANISM: Artificial sequence
<220> FEATURE:
<223> OTHER INFORMATION: Primer OK2 (HuVK2)

<400> SEQUENCE: 2
gatgttgtga tgactcagtc tcc                                              23

<210> SEQ ID NO 3
<211> LENGTH: 23
<212> TYPE: DNA
<213> ORGANISM: Artificial sequence
<220> FEATURE:
<223> OTHER INFORMATION: Primer OK3 (HuVK2B2)

<400> SEQUENCE: 3
gatattgtga tgacccagac tcc                                              23

<210> SEQ ID NO 4
<211> LENGTH: 23
<212> TYPE: DNA
<213> ORGANISM: Artificial sequence
<220> FEATURE:
<223> OTHER INFORMATION: Primer OK4 (HuVK3B)

<400> SEQUENCE: 4
gaaattgtgw tgacrcagtc tcc                                              23

<210> SEQ ID NO 5
<211> LENGTH: 23
<212> TYPE: DNA
<213> ORGANISM: Artificial sequence
<220> FEATURE:
<223> OTHER INFORMATION: Primer OK5 (HuVK5)

<400> SEQUENCE: 5
gaaacgacac tcacgcagtc tcc                                              23
```

```
<210> SEQ ID NO 6
<211> LENGTH: 23
<212> TYPE: DNA
<213> ORGANISM: Artificial sequence
<220> FEATURE:
<223> OTHER INFORMATION: Primer OK6 (HuVK6)

<400> SEQUENCE: 6
gaaattgtgc tgactcagtc tcc                                              23

<210> SEQ ID NO 7
<211> LENGTH: 24
<212> TYPE: DNA
<213> ORGANISM: Artificial sequence
<220> FEATURE:
<223> OTHER INFORMATION: Primer OCK (HuCK)

<400> SEQUENCE: 7
acactctccc ctgttgaagc tctt                                             24

<210> SEQ ID NO 8
<211> LENGTH: 23
<212> TYPE: DNA
<213> ORGANISM: Artificial sequence
<220> FEATURE:
<223> OTHER INFORMATION: Primer OL1 (HuVL1A)

<400> SEQUENCE: 8
cagtctgtgc tgactcagcc acc                                              23

<210> SEQ ID NO 9
<211> LENGTH: 23
<212> TYPE: DNA
<213> ORGANISM: Artificial sequence
<220> FEATURE:
<223> OTHER INFORMATION: Primer OL1 (HuVL1B)

<400> SEQUENCE: 9
cagtctgtgy tgacgcagcc gcc                                              23

<210> SEQ ID NO 10
<211> LENGTH: 23
<212> TYPE: DNA
<213> ORGANISM: Artificial sequence
<220> FEATURE:
<223> OTHER INFORMATION: Primer OL1 (HuVL1C)

<400> SEQUENCE: 10
cagtctgtcg tgacgcagcc gcc                                              23

<210> SEQ ID NO 11
<211> LENGTH: 20
<212> TYPE: DNA
<213> ORGANISM: Artificial sequence
<220> FEATURE:
<223> OTHER INFORMATION: Primer OL2 (HuVL2B)

<400> SEQUENCE: 11
cagtctgccc tgactcagcc                                                  20

<210> SEQ ID NO 12
<211> LENGTH: 23
<212> TYPE: DNA
<213> ORGANISM: Artificial sequence
<220> FEATURE:
<223> OTHER INFORMATION: Primer OL3 (HuVL3A)
```

<210> SEQ ID NO 12
<211> LENGTH: 23
<212> TYPE: DNA
<213> ORGANISM: Artificial sequence
<220> FEATURE:
<223> OTHER INFORMATION: Primer OL3 (HuVL3A)

<400> SEQUENCE: 12
tcctatgwgc tgactcagcc acc                                          23

<210> SEQ ID NO 13
<211> LENGTH: 23
<212> TYPE: DNA
<213> ORGANISM: Artificial sequence
<220> FEATURE:
<223> OTHER INFORMATION: Primer OL4 (HuVL3B)

<400> SEQUENCE: 13
tcttctgagc tgactcagga ccc                                          23

<210> SEQ ID NO 14
<211> LENGTH: 20
<212> TYPE: DNA
<213> ORGANISM: Artificial sequence
<220> FEATURE:
<223> OTHER INFORMATION: Primer OL5 (HuVL4B)

<400> SEQUENCE: 14
cagcytgtgc tgactcaatc                                              20

<210> SEQ ID NO 15
<211> LENGTH: 23
<212> TYPE: DNA
<213> ORGANISM: Artificial sequence
<220> FEATURE:
<223> OTHER INFORMATION: Primer OL6 (HuVL5)

<400> SEQUENCE: 15
caggctgtgc tgactcagcc gtc                                          23

<210> SEQ ID NO 16
<211> LENGTH: 23
<212> TYPE: DNA
<213> ORGANISM: Artificial sequence
<220> FEATURE:
<223> OTHER INFORMATION: Primer OL7 (HuVL6)

<400> SEQUENCE: 16
aattttatgc tgactcagcc cca                                          23

<210> SEQ ID NO 17
<211> LENGTH: 23
<212> TYPE: DNA
<213> ORGANISM: Artificial sequence
<220> FEATURE:
<223> OTHER INFORMATION: Primer OL8 (HuVL7/8)

<400> SEQUENCE: 17
cagrctgtgg tgacycagga gcc                                          23

<210> SEQ ID NO 18
<211> LENGTH: 23
<212> TYPE: DNA
<213> ORGANISM: Artificial sequence
<220> FEATURE:
<223> OTHER INFORMATION: Primer OL9 (HuVL9)

<400> SEQUENCE: 18
cwgcctgtgc tgactcagcc mcc                                          23

<210> SEQ ID NO 19
<211> LENGTH: 18

```
<212> TYPE: DNA
<213> ORGANISM: Artificial sequence
<220> FEATURE:
<223> OTHER INFORMATION: Primer OL9 (HuVL10)

<400> SEQUENCE: 19
caggcagggc tgactcag                                                 18

<210> SEQ ID NO 20
<211> LENGTH: 23
<212> TYPE: DNA
<213> ORGANISM: Artificial sequence
<220> FEATURE:
<223> OTHER INFORMATION: Primer OCL (HuCL2)

<400> SEQUENCE: 20
tgaacattct gtaggggcca ctg                                           23

<210> SEQ ID NO 21
<211> LENGTH: 23
<212> TYPE: DNA
<213> ORGANISM: Artificial sequence
<220> FEATURE:
<223> OTHER INFORMATION: Primer OCL (HuCL7)

<400> SEQUENCE: 21
agagcattct gcaggggcca ctg                                           23

<210> SEQ ID NO 22
<211> LENGTH: 23
<212> TYPE: DNA
<213> ORGANISM: Artificial sequence
<220> FEATURE:
<223> OTHER INFORMATION: Primer OH1 (HuVH1B7A)

<400> SEQUENCE: 22
cagrtgcagc tggtgcartc tgg                                           23

<210> SEQ ID NO 23
<211> LENGTH: 23
<212> TYPE: DNA
<213> ORGANISM: Artificial sequence
<220> FEATURE:
<223> OTHER INFORMATION: Primer OH1 (HuVH1C)

<400> SEQUENCE: 23
saggtccagc tggtrcagtc tgg                                           23

<210> SEQ ID NO 24
<211> LENGTH: 23
<212> TYPE: DNA
<213> ORGANISM: Artificial sequence
<220> FEATURE:
<223> OTHER INFORMATION: Primer OH2 (HuVH2B)

<400> SEQUENCE: 24
cagrtcacct tgaaggagtc tgg                                           23

<210> SEQ ID NO 25
<211> LENGTH: 18
<212> TYPE: DNA
<213> ORGANISM: Artificial sequence
<220> FEATURE:
<223> OTHER INFORMATION: Primer OH3 (HuVH3A)

<400> SEQUENCE: 25
gaggtgcagc tggtggag                                                 18
```

<210> SEQ ID NO 26
<211> LENGTH: 23
<212> TYPE: DNA
<213> ORGANISM: Artificial sequence
<220> FEATURE:
<223> OTHER INFORMATION: Primer OH4 (HuVH3C)

<400> SEQUENCE: 26
gaggtgcagc tggtggagwc ygg                                    23

<210> SEQ ID NO 27
<211> LENGTH: 23
<212> TYPE: DNA
<213> ORGANISM: Artificial sequence
<220> FEATURE:
<223> OTHER INFORMATION: Primer OH5 (HuVH4B)

<400> SEQUENCE: 27
caggtgcagc tacagcagtg ggg                                    23

<210> SEQ ID NO 28
<211> LENGTH: 23
<212> TYPE: DNA
<213> ORGANISM: Artificial sequence
<220> FEATURE:
<223> OTHER INFORMATION: Primer OH6 (HuVH4C)

<400> SEQUENCE: 28
cagstgcagc tgcaggagtc sgg                                    23

<210> SEQ ID NO 29
<211> LENGTH: 23
<212> TYPE: DNA
<213> ORGANISM: Artificial sequence
<220> FEATURE:
<223> OTHER INFORMATION: Primer OH7 (HuVH6A)

<400> SEQUENCE: 29
caggtacagc tgcagcagtc agg                                    23

<210> SEQ ID NO 30
<211> LENGTH: 24
<212> TYPE: DNA
<213> ORGANISM: Artificial sequence
<220> FEATURE:
<223> OTHER INFORMATION: Primer OCG (HuCIgG)

<400> SEQUENCE: 30
gtccaccttg gtgttgctgg gctt                                   24

<210> SEQ ID NO 31
<211> LENGTH: 24
<212> TYPE: DNA
<213> ORGANISM: Artificial sequence
<220> FEATURE:
<223> OTHER INFORMATION: Primer OCM (HuCIgM)

<400> SEQUENCE: 31
tggaagaggc acgttctttt cttt                                   24

<210> SEQ ID NO 32
<211> LENGTH: 41
<212> TYPE: DNA
<213> ORGANISM: Artificial sequence
<220> FEATURE:
<223> OTHER INFORMATION: Primer OK1S (HuVK1B-SAL)

-continued

<400> SEQUENCE: 32
tgagcacaca ggtcgacgga catccagwtg acccagtctc c                41

<210> SEQ ID NO 33
<211> LENGTH: 41
<212> TYPE: DNA
<213> ORGANISM: Artificial sequence
<220> FEATURE:
<223> OTHER INFORMATION: Primer OK2S (HuVK2-SAL)

<400> SEQUENCE: 33
tgagcacaca ggtcgacgga tgttgtgatg actcagtctc c                41

<210> SEQ ID NO 34
<211> LENGTH: 41
<212> TYPE: DNA
<213> ORGANISM: Artificial sequence
<220> FEATURE:
<223> OTHER INFORMATION: Primer OK3S (HuVK2B2-SAL)

<400> SEQUENCE: 34
tgagcacaca ggtcgacgga tattgtgatg acccagactc c                41

<210> SEQ ID NO 35
<211> LENGTH: 41
<212> TYPE: DNA
<213> ORGANISM: Artificial sequence
<220> FEATURE:
<223> OTHER INFORMATION: Primer OK4S (HuVK3B-SAL)

<400> SEQUENCE: 35
tgagcacaca ggtcgacgga aattgtgwtg acrcagtctc c                41

<210> SEQ ID NO 36
<211> LENGTH: 41
<212> TYPE: DNA
<213> ORGANISM: Artificial sequence
<220> FEATURE:
<223> OTHER INFORMATION: Primer OK5S (HuVK5-SAL)

<400> SEQUENCE: 36
tgagcacaca ggtcgacgga aacgacactc acgcagtctc c                41

<210> SEQ ID NO 37
<211> LENGTH: 41
<212> TYPE: DNA
<213> ORGANISM: Artificial sequence
<220> FEATURE:
<223> OTHER INFORMATION: Primer OK6S (HuVK6-SAL)

<400> SEQUENCE: 37
tgagcacaca ggtcgacgga aattgtgctg actcagtctc c                41

<210> SEQ ID NO 38
<211> LENGTH: 48
<212> TYPE: DNA
<213> ORGANISM: Artificial sequence
<220> FEATURE:
<223> OTHER INFORMATION: Primer OJK1 (HuJK1-NOT)

<400> SEQUENCE: 38
gagtcattct cgacttgcgg ccgcacgttt gatttccacc ttggtccc        48

<210> SEQ ID NO 39
<211> LENGTH: 48

<212> TYPE: DNA
<213> ORGANISM: Artificial sequence
<220> FEATURE:
<223> OTHER INFORMATION: Primer OJK2 (HuJK2-NOT)

<400> SEQUENCE: 39
gagtcattct cgacttgcgg ccgcacgttt gatctccagc ttggtccc         48

<210> SEQ ID NO 40
<211> LENGTH: 48
<212> TYPE: DNA
<213> ORGANISM: Artificial sequence
<220> FEATURE:
<223> OTHER INFORMATION: Primer OJK3 (HuJK3-NOT)

<400> SEQUENCE: 40
gagtcattct cgacttgcgg ccgcacgttt gatatccact ttggtccc         48

<210> SEQ ID NO 41
<211> LENGTH: 48
<212> TYPE: DNA
<213> ORGANISM: Artificial sequence
<220> FEATURE:
<223> OTHER INFORMATION: Primer OJK4 (HuJK4-NOT)

<400> SEQUENCE: 41
gagtcattct cgacttgcgg ccgcacgttt gatctccacc ttggtccc         48

<210> SEQ ID NO 42
<211> LENGTH: 48
<212> TYPE: DNA
<213> ORGANISM: Artificial sequence
<220> FEATURE:
<223> OTHER INFORMATION: Primer OJK5 (HuJK5-NOT)

<400> SEQUENCE: 42
gagtcattct cgacttgcgg ccgcacgttt aatctccagt cgtgtccc         48

<210> SEQ ID NO 43
<211> LENGTH: 41
<212> TYPE: DNA
<213> ORGANISM: Artificial sequence
<220> FEATURE:
<223> OTHER INFORMATION: Primer OL1S (HuVL1A-SAL)

<400> SEQUENCE: 43
tgagcacaca ggtcgacgca gtctgtgctg actcagccac c               41

<210> SEQ ID NO 44
<211> LENGTH: 41
<212> TYPE: DNA
<213> ORGANISM: Artificial sequence
<220> FEATURE:
<223> OTHER INFORMATION: Primer OL1S (HuVL1B-SAL)

<400> SEQUENCE: 44
tgagcacaca ggtcgacgca gtctgtgytg acgcagccgc c               41

<210> SEQ ID NO 45
<211> LENGTH: 41
<212> TYPE: DNA
<213> ORGANISM: Artificial sequence
<220> FEATURE:
<223> OTHER INFORMATION: Primer OL1S (HuVL1C-SAL)

<400> SEQUENCE: 45
tgagcacaca ggtcgacgca gtctgtcgtg acgcagccgc c               41

<210> SEQ ID NO 46
<211> LENGTH: 38
<212> TYPE: DNA
<213> ORGANISM: Artificial sequence
<220> FEATURE:
<223> OTHER INFORMATION: Primer OL2S (HuVL2B-SAL)

<400> SEQUENCE: 46
tgagcacaca ggtcgacgca gtctgccctg actcagcc                                38

<210> SEQ ID NO 47
<211> LENGTH: 41
<212> TYPE: DNA
<213> ORGANISM: Artificial sequence
<220> FEATURE:
<223> OTHER INFORMATION: Primer OL3S (HuVL3A-SAL)

<400> SEQUENCE: 47
tgagcacaca ggtcgacgtc ctatgwgctg actcagccac c                            41

<210> SEQ ID NO 48
<211> LENGTH: 41
<212> TYPE: DNA
<213> ORGANISM: Artificial sequence
<220> FEATURE:
<223> OTHER INFORMATION: Primer OL4S (HuVL3B-SAL)

<400> SEQUENCE: 48
tgagcacaca ggtcgacgtc ttctgagctg actcaggacc c                            41

<210> SEQ ID NO 49
<211> LENGTH: 38
<212> TYPE: DNA
<213> ORGANISM: Artificial sequence
<220> FEATURE:
<223> OTHER INFORMATION: Primer OL5S (HuVL4B-SAL)

<400> SEQUENCE: 49
tgagcacaca ggtcgacgca gcytgtgctg actcaatc                                38

<210> SEQ ID NO 50
<211> LENGTH: 41
<212> TYPE: DNA
<213> ORGANISM: Artificial sequence
<220> FEATURE:
<223> OTHER INFORMATION: Primer OL6S (HuVL5-SAL)

<400> SEQUENCE: 50
tgagcacaca ggtcgacgca ggctgtgctg actcagccgt c                            41

<210> SEQ ID NO 51
<211> LENGTH: 41
<212> TYPE: DNA
<213> ORGANISM: Artificial sequence
<220> FEATURE:
<223> OTHER INFORMATION: Primer OL7S (HuVL6-SAL)

<400> SEQUENCE: 51
tgagcacaca ggtcgacgaa ttttatgctg actcagcccc a                            41

<210> SEQ ID NO 52
<211> LENGTH: 41
<212> TYPE: DNA
<213> ORGANISM: Artificial sequence
<220> FEATURE:
<223> OTHER INFORMATION: Primer OL8S (HuVL7/8-SAL)

<400> SEQUENCE: 52
tgagcacaca ggtcgacgca grctgtggtg acycaggagc c                41

<210> SEQ ID NO 53
<211> LENGTH: 41
<212> TYPE: DNA
<213> ORGANISM: Artificial sequence
<220> FEATURE:
<223> OTHER INFORMATION: Primer OL9S (HuVL9-SAL)

<400> SEQUENCE: 53
tgagcacaca ggtcgacgcw gcctgtgctg actcagccmc c                41

<210> SEQ ID NO 54
<211> LENGTH: 36
<212> TYPE: DNA
<213> ORGANISM: Artificial sequence
<220> FEATURE:
<223> OTHER INFORMATION: Primer OL9S (HuVL10-SAL)

<400> SEQUENCE: 54
tgagcacaca ggtcgacgca ggcagggctg actcag                      36

<210> SEQ ID NO 55
<211> LENGTH: 48
<212> TYPE: DNA
<213> ORGANISM: Artificial sequence
<220> FEATURE:
<223> OTHER INFORMATION: Primer OJL1 (HuJL1-NOT)

<400> SEQUENCE: 55
gagtcattct cgacttgcgg ccgcacctag gacggtgacc ttggtccc         48

<210> SEQ ID NO 56
<211> LENGTH: 48
<212> TYPE: DNA
<213> ORGANISM: Artificial sequence
<220> FEATURE:
<223> OTHER INFORMATION: Primer OJL2 (HuJL2/3-NOT)

<400> SEQUENCE: 56
gagtcattct cgacttgcgg ccgcacctag gacggtcagc ttggtccc         48

<210> SEQ ID NO 57
<211> LENGTH: 48
<212> TYPE: DNA
<213> ORGANISM: Artificial sequence
<220> FEATURE:
<223> OTHER INFORMATION: Primer OJL3 (HuJL7-NOT)

<400> SEQUENCE: 57
gagtcattct cgacttgcgg ccgcaccgag gacggtcagc tgggtgcc         48

<210> SEQ ID NO 58
<211> LENGTH: 56
<212> TYPE: DNA
<213> ORGANISM: Artificial sequence
<220> FEATURE:
<223> OTHER INFORMATION: Primer OH1S (HuVH1B-SFI)

<400> SEQUENCE: 58
gtcctcgcaa ctgcggccca gccggccatg gcccagrtgc agctggtgca rtctgg   56

<210> SEQ ID NO 59
<211> LENGTH: 56

```
<212> TYPE: DNA
<213> ORGANISM: Artificial sequence
<220> FEATURE:
<223> OTHER INFORMATION: Primer OH1S (HuVH1C-SFI)

<400> SEQUENCE: 59
gtcctcgcaa ctgcggccca gccggccatg gccsaggtcc agctggtrca gtctgg        56

<210> SEQ ID NO 60
<211> LENGTH: 56
<212> TYPE: DNA
<213> ORGANISM: Artificial sequence
<220> FEATURE:
<223> OTHER INFORMATION: Primer OH2S (HuVH2B-SFI)

<400> SEQUENCE: 60
gtcctcgcaa ctgcggccca gccggccatg gcccagrtca ccttgaagga gtctgg        56

<210> SEQ ID NO 61
<211> LENGTH: 51
<212> TYPE: DNA
<213> ORGANISM: Artificial sequence
<220> FEATURE:
<223> OTHER INFORMATION: Primer OH3S (HuVH3A-SFI)

<400> SEQUENCE: 61
gtcctcgcaa ctgcggccca gccggccatg gccgaggtgc agctggtgga g             51

<210> SEQ ID NO 62
<211> LENGTH: 56
<212> TYPE: DNA
<213> ORGANISM: Artificial sequence
<220> FEATURE:
<223> OTHER INFORMATION: Primer OH4S (HuVH3C-SFI)

<400> SEQUENCE: 62
gtcctcgcaa ctgcggccca gccggccatg gccgaggtgc agctggtgga gwcygg        56

<210> SEQ ID NO 63
<211> LENGTH: 56
<212> TYPE: DNA
<213> ORGANISM: Artificial sequence
<220> FEATURE:
<223> OTHER INFORMATION: Primer OH5S (HuVH4B-SFI)

<400> SEQUENCE: 63
gtcctcgcaa ctgcggccca gccggccatg gcccaggtgc agctacagca gtgggg        56

<210> SEQ ID NO 64
<211> LENGTH: 56
<212> TYPE: DNA
<213> ORGANISM: Artificial sequence
<220> FEATURE:
<223> OTHER INFORMATION: Primer OH6S (HuVH4C-SFI)

<400> SEQUENCE: 64
gtcctcgcaa ctgcggccca gccggccatg gcccagstgc agctgcagga gtcsgg        56

<210> SEQ ID NO 65
<211> LENGTH: 56
<212> TYPE: DNA
<213> ORGANISM: Artificial sequence
<220> FEATURE:
<223> OTHER INFORMATION: Primer OH7S (HuVH6A-SFI)

<400> SEQUENCE: 65
gtcctcgcaa ctgcggccca gccggccatg gcccaggtac agctgcagca gtcagg        56
```

<210> SEQ ID NO 66
<211> LENGTH: 36
<212> TYPE: DNA
<213> ORGANISM: Artificial sequence
<220> FEATURE:
<223> OTHER INFORMATION: Primer OJH1 (HuJH1/2-XHO)

<400> SEQUENCE: 66
gagtcattct cgactcgaga crgtgaccag ggtgcc                       36

<210> SEQ ID NO 67
<211> LENGTH: 36
<212> TYPE: DNA
<213> ORGANISM: Artificial sequence
<220> FEATURE:
<223> OTHER INFORMATION: Primer OJH2 (HuJH3-XHO)

<400> SEQUENCE: 67
gagtcattct cgactcgaga cggtgaccat tgtccc                       36

<210> SEQ ID NO 68
<211> LENGTH: 36
<212> TYPE: DNA
<213> ORGANISM: Artificial sequence
<220> FEATURE:
<223> OTHER INFORMATION: Primer OJH3 (HuJH4/5-XHO)

<400> SEQUENCE: 68
gagtcattct cgactcgaga cggtgaccag ggttcc                       36

<210> SEQ ID NO 69
<211> LENGTH: 36
<212> TYPE: DNA
<213> ORGANISM: Artificial sequence
<220> FEATURE:
<223> OTHER INFORMATION: Primer OJH4 (HuJH6-XHO)

<400> SEQUENCE: 69
gagtcattct cgactcgaga cggtgaccgt ggtccc                       36

<210> SEQ ID NO 70
<211> LENGTH: 741
<212> TYPE: DNA
<213> ORGANISM: Homo sapiens
<220> FEATURE:
<221> NAME/KEY: CDS
<222> LOCATION: (1)..(741)
<223> OTHER INFORMATION:

<400> SEQUENCE: 70

| | | | | | | | | | | | | | | | | |
|---|---|---|---|---|---|---|---|---|---|---|---|---|---|---|---|---|
| gag | gtg | cag | ctg | gtg | gag | tct | ggg | gga | ggc | ctg | gtc | aag | cct | gag | ggg | 48 |
| Glu | Val | Gln | Leu | Val | Glu | Ser | Gly | Gly | Gly | Leu | Val | Lys | Pro | Glu | Gly | |
| 1 | | | | 5 | | | | | 10 | | | | | 15 | | |
| tcc | ctg | aga | ctc | tcc | tgt | gca | gcc | tct | gga | ttc | acc | ttc | agt | agc | tat | 96 |
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |
| agc | atg | aac | tgg | gtc | cgc | cag | gct | cca | ggg | aag | ggg | ctg | gag | tgg | gtc | 144 |
| Ser | Met | Asn | Trp | Val | Arg | Gln | Ala | Pro | Gly | Lys | Gly | Leu | Glu | Trp | Val | |
| | | 35 | | | | | 40 | | | | | 45 | | | | |
| tca | tcc | att | tct | agc | ggt | ggt | ggt | tac | ata | aac | tac | gca | gac | tca | ctg | 192 |
| Ser | Ser | Ile | Ser | Ser | Gly | Gly | Gly | Tyr | Ile | Asn | Tyr | Ala | Asp | Ser | Leu | |
| 50 | | | | | 55 | | | | | 60 | | | | | | |
| aag | ggc | cga | ttc | acc | atc | tcc | aga | gac | aac | gcc | aaa | aac | tca | ctg | ttt | 240 |
| Lys | Gly | Arg | Phe | Thr | Ile | Ser | Arg | Asp | Asn | Ala | Lys | Asn | Ser | Leu | Phe | |
| 65 | | | | | 70 | | | | | 75 | | | | | 80 | |

```
ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                85                  90                  95 gcg aga gga aga gga tat tgt agt ggt ggt gtg tgc tac gtc gac tac      336
Ala Arg Gly Arg Gly Tyr Cys Ser Gly Gly Val Cys Tyr Val Asp Tyr
            100                 105                 110 tgg ggc cag gga acc ctg gtc acc gtc tcg agc ggt acg ggc ggt tca      384
Trp Gly Gln Gly Thr Leu Val Thr Val Ser Ser Gly Thr Gly Gly Ser
        115                 120                 125 ggc gga acc ggc agc ggc act ggc ggg tcg acg gaa att gtg ctg act      432
Gly Gly Thr Gly Ser Gly Thr Gly Gly Ser Thr Glu Ile Val Leu Thr
    130                 135                 140 cag tct cca gcc acc ctg tct ttg tct cca ggg gaa aga gcc acc ctc      480
Gln Ser Pro Ala Thr Leu Ser Leu Ser Pro Gly Glu Arg Ala Thr Leu
145                 150                 155                 160 tcc tgc agg gcc agt cag agt gtc agc agc tcc tta gcc tgg tac caa      528
Ser Cys Arg Ala Ser Gln Ser Val Ser Ser Ser Leu Ala Trp Tyr Gln
                165                 170                 175 cag aaa cct ggc cag gct ccc agg ctc ctc atc tat gat gct tcc aac      576
Gln Lys Pro Gly Gln Ala Pro Arg Leu Leu Ile Tyr Asp Ala Ser Asn
            180                 185                 190 agg gcc gct ggc atc cca gcc agg ttc agt ggc agt ggg tct ggg aca      624
Arg Ala Ala Gly Ile Pro Ala Arg Phe Ser Gly Ser Gly Ser Gly Thr
        195                 200                 205 gac ttc act ctc acc atc ggc aga ctg gag cct gaa gat ttt gca gtg      672
Asp Phe Thr Leu Thr Ile Gly Arg Leu Glu Pro Glu Asp Phe Ala Val
    210                 215                 220 tat tac tgt cag cag tat ggt agc tca ccg tgg acg ttc ggc caa ggg      720
Tyr Tyr Cys Gln Gln Tyr Gly Ser Ser Pro Trp Thr Phe Gly Gln Gly
225                 230                 235                 240 acc aag gtg gaa atc aaa cgt                                          741
Thr Lys Val Glu Ile Lys Arg
            245

<210> SEQ ID NO 71
<211> LENGTH: 247
<212> TYPE: PRT
<213> ORGANISM: Homo sapiens

<400> SEQUENCE: 71

Glu Val Gln Leu Val Glu Ser Gly Gly Gly Leu Val Lys Pro Glu Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Gly Gly Gly Tyr Ile Asn Tyr Ala Asp Ser Leu
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Arg Gly Tyr Cys Ser Gly Gly Val Cys Tyr Val Asp Tyr
            100                 105                 110

Trp Gly Gln Gly Thr Leu Val Thr Val Ser Ser Gly Thr Gly Gly Ser
        115                 120                 125

Gly Gly Thr Gly Ser Gly Thr Gly Gly Ser Thr Glu Ile Val Leu Thr
    130                 135                 140
```

```
Gln Ser Pro Ala Thr Leu Ser Leu Ser Pro Gly Glu Arg Ala Thr Leu
145                 150                 155                 160

Ser Cys Arg Ala Ser Gln Ser Val Ser Ser Leu Ala Trp Tyr Gln
                165                 170                 175

Gln Lys Pro Gly Gln Ala Pro Arg Leu Leu Ile Tyr Asp Ala Ser Asn
            180                 185                 190

Arg Ala Ala Gly Ile Pro Ala Arg Phe Ser Gly Ser Gly Ser Gly Thr
        195                 200                 205

Asp Phe Thr Leu Thr Ile Gly Arg Leu Glu Pro Glu Asp Phe Ala Val
        210                 215                 220

Tyr Tyr Cys Gln Gln Tyr Gly Ser Ser Pro Trp Thr Phe Gly Gln Gly
225                 230                 235                 240

Thr Lys Val Glu Ile Lys Arg
            245
```

<210> SEQ ID NO 72
<211> LENGTH: 121
<212> TYPE: PRT
<213> ORGANISM: homo sapiens

<400> SEQUENCE: 72

```
Glu Val Gln Leu Val Glu Ser Gly Gly Gly Leu Val Lys Pro Glu Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Gly Gly Gly Tyr Ile Asn Tyr Ala Asp Ser Leu
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Arg Gly Tyr Cys Ser Gly Gly Val Cys Tyr Val Asp Tyr
            100                 105                 110

Trp Gly Gln Gly Thr Leu Val Thr Val
        115                 120
```

<210> SEQ ID NO 73
<211> LENGTH: 108
<212> TYPE: PRT
<213> ORGANISM: homo sapiens

<400> SEQUENCE: 73

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ala Gly Ile Pro Ala Arg Phe Ser Gly
    50                  55                  60

Ser Gly Ser Gly Thr Asp Phe Thr Leu Thr Ile Gly Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys Arg
```

100             105

<210> SEQ ID NO 74
<211> LENGTH: 14
<212> TYPE: PRT
<213> ORGANISM: homo sapiens

<400> SEQUENCE: 74

Gly Arg Gly Tyr Cys Ser Gly Gly Val Cys Tyr Val Asp Tyr
1               5                   10

<210> SEQ ID NO 75
<211> LENGTH: 17
<212> TYPE: PRT
<213> ORGANISM: Homo sapiens

<400> SEQUENCE: 75

Ser Ile Ser Ser Gly Gly Gly Tyr Ile Asn Tyr Ala Asp Ser Leu Lys
1               5                   10                  15

Gly

<210> SEQ ID NO 76
<211> LENGTH: 5
<212> TYPE: PRT
<213> ORGANISM: homo sapiens

<400> SEQUENCE: 76

Ser Tyr Ser Met Asn
1               5

<210> SEQ ID NO 77
<211> LENGTH: 9
<212> TYPE: PRT
<213> ORGANISM: homo sapiens

<400> SEQUENCE: 77

Gln Gln Tyr Gly Ser Ser Pro Trp Thr
1               5

<210> SEQ ID NO 78
<211> LENGTH: 7
<212> TYPE: PRT
<213> ORGANISM: homo sapiens

<400> SEQUENCE: 78

Asp Ala Ser Asn Arg Ala Ala
1               5

<210> SEQ ID NO 79
<211> LENGTH: 11
<212> TYPE: PRT
<213> ORGANISM: homo sapiens

<400> SEQUENCE: 79

Arg Ala Ser Gln Ser Val Ser Ser Ser Leu Ala
1               5                   10

<210> SEQ ID NO 80
<211> LENGTH: 1359
<212> TYPE: DNA
<213> ORGANISM: homo sapiens
<220> FEATURE:
<221> NAME/KEY: CDS
<222> LOCATION: (1)..(1359)
<223> OTHER INFORMATION:

<400> SEQUENCE: 80

```
gag gtg cag ctg gtg gag tct ggg gga ggc ctg gtc aag cct gag ggg      48
Glu Val Gln Leu Val Glu Ser Gly Gly Gly Leu Val Lys Pro Glu Gly
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 agc atg aac tgg gtc cgc cag gct cca ggg aag ggg ctg gag tgg gtc     144
Ser Met Asn Trp Val Arg Gln Ala Pro Gly Lys Gly Leu Glu Trp Val
        35                  40                  45 tca tcc att tct agc ggt ggt ggt tac ata aac tac gca gac tca ctg     192
Ser Ser Ile Ser Ser Gly Gly Gly Tyr Ile Asn Tyr Ala Asp Ser Leu
    50                  55                  60 aag ggc cga ttc acc atc tcc aga gac aac gcc aaa aac tca ctg ttt     240
Lys Gly Arg Phe Thr Ile Ser Arg Asp Asn Ala Lys Asn Ser Leu Phe
65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                85                  90                  95 gcg aga gga aga gga tat tgt agt ggt ggt gtg tgc tac gtc gac tac     336
Ala Arg Gly Arg Gly Tyr Cys Ser Gly Gly Val Cys Tyr Val Asp Tyr
            100                 105                 110 tgg ggc cag gga acc ctg gtc acc gtc tcg agt gct agc acc aag ggc     384
Trp Gly Gln Gly Thr Leu Val Thr Val Ser Ser Ala Ser Thr Lys Gly
        115                 120                 125 ccc agc gtg ttc ccc ctg gcc ccc agc agc aag agc acc agc ggc ggc     432
Pro Ser Val Phe Pro Leu Ala Pro Ser Ser Lys Ser Thr Ser Gly Gly
    130                 135                 140 aca gcc gcc ctg ggc tgc ctg gtg aag gac tac ttc ccc gag ccc gtg     480
Thr Ala Ala Leu Gly Cys Leu Val Lys Asp Tyr Phe Pro Glu Pro Val
145                 150                 155                 160 acc gtg agc tgg aac agc ggc gcc ttg acc agc ggc gtg cac acc ttc     528
Thr Val Ser Trp Asn Ser Gly Ala Leu Thr Ser Gly Val His Thr Phe
                165                 170                 175 ccc gcc gtg ctg cag agc agc ggc ctg tac agc ctg agc agc gtg gtg     576
Pro Ala Val Leu Gln Ser Ser Gly Leu Tyr Ser Leu Ser Ser Val Val
            180                 185                 190 acc gtg ccc agc agc agc ctg ggc acc cag acc tac atc tgc aac gtg     624
Thr Val Pro Ser Ser Ser Leu Gly Thr Gln Thr Tyr Ile Cys Asn Val
        195                 200                 205 aac cac aag ccc agc aac acc aag gtg gac aaa cgc gtg gag ccc aag     672
Asn His Lys Pro Ser Asn Thr Lys Val Asp Lys Arg Val Glu Pro Lys
    210                 215                 220 agc tgc gac aag acc cac acc tgc ccc ccc tgc cct gcc ccc gag ctg     720
Ser Cys Asp Lys Thr His Thr Cys Pro Pro Cys Pro Ala Pro Glu Leu
225                 230                 235                 240 ctg ggc gga ccc tcc gtg ttc ctg ttc ccc ccc aag ccc aag gac acc     768
Leu Gly Gly Pro Ser Val Phe Leu Phe Pro Pro Lys Pro Lys Asp Thr
                245                 250                 255 ctc atg atc agc cgg acc ccc gag gtg acc tgc gtg gtg gtg gac gtg     816
Leu Met Ile Ser Arg Thr Pro Glu Val Thr Cys Val Val Val Asp Val
            260                 265                 270 agc cac gag gac ccc gag gtg aag ttc aac tgg tac gtg gac ggc gtg     864
Ser His Glu Asp Pro Glu Val Lys Phe Asn Trp Tyr Val Asp Gly Val
        275                 280                 285 gag gtg cac aac gcc aag acc aag ccc cgg gag gag cag tac aac agc     912
Glu Val His Asn Ala Lys Thr Lys Pro Arg Glu Glu Gln Tyr Asn Ser
    290                 295                 300 acc tac cgg gtg gtg agc gtg ctc acc gtg ctg cac cag gac tgg ctg     960
Thr Tyr Arg Val Val Ser Val Leu Thr Val Leu His Gln Asp Trp Leu
```

```
                305                 310                 315                 320
aac ggc aag gag tac aag tgc aag gtg agc aac aag gcc ctg cct gcc        1008
Asn Gly Lys Glu Tyr Lys Cys Lys Val Ser Asn Lys Ala Leu Pro Ala
                325                 330                 335 ccc atc gag aag acc atc agc aag gcc aag ggc cag ccc cgg gag ccc        1056
Pro Ile Glu Lys Thr Ile Ser Lys Ala Lys Gly Gln Pro Arg Glu Pro
            340                 345                 350 cag gtg tac acc ctg ccc ccc agc cgg gag gag atg acc aag aac cag        1104
Gln Val Tyr Thr Leu Pro Pro Ser Arg Glu Glu Met Thr Lys Asn Gln
        355                 360                 365 gtg tcc ctc acc tgt ctg gtg aag ggc ttc tac ccc agc gac atc gcc        1152
Val Ser Leu Thr Cys Leu Val Lys Gly Phe Tyr Pro Ser Asp Ile Ala
370                 375                 380 gtg gag tgg gag agc aac ggc cag ccc gag aac aac tac aag acc acc        1200
Val Glu Trp Glu Ser Asn Gly Gln Pro Glu Asn Asn Tyr Lys Thr Thr
385                 390                 395                 400 ccc cct gtg ctg gac agc gac ggc agc ttc ttc ctg tac agc aag ctc        1248
Pro Pro Val Leu Asp Ser Asp Gly Ser Phe Phe Leu Tyr Ser Lys Leu
                405                 410                 415 acc gtg gac aag agc cgg tgg cag cag ggc aac gtg ttc agc tgc agc        1296
Thr Val Asp Lys Ser Arg Trp Gln Gln Gly Asn Val Phe Ser Cys Ser
            420                 425                 430 gtg atg cac gag gcc ctg cac aac cac tac acc cag aag agc ctg agc        1344
Val Met His Glu Ala Leu His Asn His Tyr Thr Gln Lys Ser Leu Ser
        435                 440                 445 ctg agc ccc ggc aag                                                    1359
Leu Ser Pro Gly Lys
    450

<210> SEQ ID NO 81
<211> LENGTH: 453
<212> TYPE: PRT
<213> ORGANISM: homo sapiens

<400> SEQUENCE: 81

Glu Val Gln Leu Val Glu Ser Gly Gly Gly Leu Val Lys Pro Glu Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Gly Gly Gly Tyr Ile Asn Tyr Ala Asp Ser Leu
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Arg Gly Tyr Cys Ser Gly Gly Val Cys Tyr Val Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
                          180                185                190
Thr Val Pro Ser Ser Leu Gly Thr Gln Thr Tyr Ile Cys Asn Val
            195                200                205
Asn His Lys Pro Ser Asn Thr Lys Val Asp Lys Arg Val Glu Pro Lys
    210                215                220
Ser Cys Asp Lys Thr His Thr Cys Pro Pro Cys Pro Ala Pro Glu Leu
225                230                235                240
Leu Gly Gly Pro Ser Val Phe Leu Phe Pro Pro Lys Pro Lys Asp Thr
                245                250                255
Leu Met Ile Ser Arg Thr Pro Glu Val Thr Cys Val Val Val Asp Val
            260                265                270
Ser His Glu Asp Pro Glu Val Lys Phe Asn Trp Tyr Val Asp Gly Val
        275                280                285
Glu Val His Asn Ala Lys Thr Lys Pro Arg Glu Glu Gln Tyr Asn Ser
    290                295                300
Thr Tyr Arg Val Val Ser Val Leu Thr Val Leu His Gln Asp Trp Leu
305                310                315                320
Asn Gly Lys Glu Tyr Lys Cys Lys Val Ser Asn Lys Ala Leu Pro Ala
                325                330                335
Pro Ile Glu Lys Thr Ile Ser Lys Ala Lys Gly Gln Pro Arg Glu Pro
            340                345                350
Gln Val Tyr Thr Leu Pro Pro Ser Arg Glu Glu Met Thr Lys Asn Gln
        355                360                365
Val Ser Leu Thr Cys Leu Val Lys Gly Phe Tyr Pro Ser Asp Ile Ala
    370                375                380
Val Glu Trp Glu Ser Asn Gly Gln Pro Glu Asn Asn Tyr Lys Thr Thr
385                390                395                400
Pro Pro Val Leu Asp Ser Asp Gly Ser Phe Phe Leu Tyr Ser Lys Leu
                405                410                415
Thr Val Asp Lys Ser Arg Trp Gln Gln Gly Asn Val Phe Ser Cys Ser
            420                425                430
Val Met His Glu Ala Leu His Asn His Tyr Thr Gln Lys Ser Leu Ser
        435                440                445
Leu Ser Pro Gly Lys
    450

<210> SEQ ID NO 82
<211> LENGTH: 639
<212> TYPE: DNA
<213> ORGANISM: homo sapiens
<220> FEATURE:
<221> NAME/KEY: CDS
<222> LOCATION: (1)..(639)
<223> OTHER INFORMATION:

<400> SEQUENCE: 82 gaa att gtg ctg act cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtc agc agc tcc      96
Glu Arg Ala Thr Leu Ser Cys Arg Ala Ser Gln Ser Val Ser Ser Ser
            20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat gct tcc aac agg gcc gct ggc atc cca gcc agg ttc agt ggc     192
Tyr Asp Ala Ser Asn Arg Ala Ala Gly Ile Pro Ala Arg Phe Ser Gly
    50                  55                  60
```

```
agt ggg tct ggg aca gac ttc act ctc acc atc ggc aga ctg gag cct    240
Ser Gly Ser Gly Thr Asp Phe Thr Leu Thr Ile Gly Arg Leu Glu Pro
 65                  70                  75                  80 gaa gat ttt gca gtg tat tac tgt cag cag tat ggt agc tca ccg tgg    288
Glu Asp Phe Ala Val Tyr Tyr Cys Gln Gln Tyr Gly Ser Ser Pro Trp
                 85                  90                  95 acg ttc ggc caa ggg acc aag gtg gaa atc aaa cgt gcg gcc gca ccc    336
Thr Phe Gly Gln Gly Thr Lys Val Glu Ile Lys Arg Ala Ala Ala Pro
            100                 105                 110 agc gtg ttc atc ttc ccc ccc tcc gac gag cag ctg aag agc ggc acc    384
Ser Val Phe Ile Phe Pro Pro Ser Asp Glu Gln Leu Lys Ser Gly Thr
        115                 120                 125 gcc agc gtg gtg tgc ctg ctg aac aac ttc tac ccc cgg gag gcc aag    432
Ala Ser Val Val Cys Leu Leu Asn Asn Phe Tyr Pro Arg Glu Ala Lys
    130                 135                 140 gtg cag tgg aag gtg gac aac gcc ctg cag agc ggc aac agc cag gag    480
Val Gln Trp Lys Val Asp Asn Ala Leu Gln Ser Gly Asn Ser Gln Glu
145                 150                 155                 160 agc gtg acc gag cag gac agc aag gac tcc acc tac agc ctg agc agc    528
Ser Val Thr Glu Gln Asp Ser Lys Asp Ser Thr Tyr Ser Leu Ser Ser
                165                 170                 175 acc ctc acc ctg agc aag gcc gac tac gag aag cac aag gtg tac gcc    576
Thr Leu Thr Leu Ser Lys Ala Asp Tyr Glu Lys His Lys Val Tyr Ala
            180                 185                 190 tgc gag gtg acc cac cag ggc ctg agc agc ccc gtg acc aag agc ttc    624
Cys Glu Val Thr His Gln Gly Leu Ser Ser Pro Val Thr Lys Ser Phe
        195                 200                 205 aac cgg ggc gag tgt                                                639
Asn Arg Gly Glu Cys
    210

<210> SEQ ID NO 83
<211> LENGTH: 213
<212> TYPE: PRT
<213> ORGANISM: homo sapiens

<400> SEQUENCE: 83

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ala Gly Ile Pro Ala Arg Phe Ser Gly
    50                  55                  60

Ser Gly Ser Gly Thr Asp Phe Thr Leu Thr Ile Gly Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys Arg Ala Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

```
                    165                 170                 175
Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 84
<211> LENGTH: 10515
<212> TYPE: DNA
<213> ORGANISM: Artificial sequence
<220> FEATURE:
<223> OTHER INFORMATION: pIg-C911-HCgamma1
<220> FEATURE:
<221> NAME/KEY: misc_feature
<222> LOCATION: (1326)..(5076)
<223> OTHER INFORMATION: Stuffer

<400> SEQUENCE: 84
tcgacggatc gggagatctc ccgatcccct atggtgcact ctcagtacaa tctgctctga      60
tgccgcatag ttaagccagt atctgctccc tgcttgtgtg ttggaggtcg ctgagtagtg     120
cgcgagcaaa atttaagcta acaaggca aggcttgacc acaattgca tgaagaatct       180 gcttaggggt aggcgttttg cgctgcttcg ctaggtggtc aatattggcc attagccata    240
ttattcattg gttatatagc ataaatcaat attggctatt ggccattgca tacgttgtat    300
ccatatcata atatgtacat ttatattggc tcatgtccaa cattaccgcc atgttgacat    360
tgattattga ctagttatta atagtaatca attacggggt cattagttca tagcccatat    420
atggagttcc gcgttacata acttacggta atggcccgc ctggctgacc gcccaacgac     480
ccccgcccat tgacgtcaat aatgacgtat gttcccatag taacgccaat agggactttc    540
cattgacgtc aatgggtgga gtatttacgg taaactgccc acttggcagt acatcaagtg    600
tatcatatgc caagtacgcc ccctattgac gtcaatgacg taaatggcc cgcctggcat     660 tatgcccagt acatgacctt atgggacttt cctacttggc agtacatcta cgtattagtc    720
atcgctatta ccatggtgat gcggttttgg cagtacatca atgggcgtgg atagcggttt    780
gactcacggg gatttccaag tctccacccc attgacgtca atgggagttt gttttggcac    840
caaaatcaac gggactttcc aaaatgtcgt aacaactccg ccccattgac gcaaatgggc    900
ggtaggcgtg tacggtggga ggtctatata agcagagctc gtttagtgaa ccgtcagatc    960
gcctggagac gccatccacg ctgttttgac ctccatagaa gacaccggga ccgatccagc   1020
ctccgcggcc gggaacggtg cattggaagc tggcctggat atcctgactc tcttaggtag   1080
ccttgcagaa gttggtcgtg aggcactggg caggtaagta tcaaggttac aagacaggtt   1140
taaggagatc aatagaaact gggcttgtcg agacagagaa gactcttgcg tttctgatag   1200
gcacctattg gtcttactga catccacttt gcctttctct ccacaggtgt ccactcccag   1260
ttcaattaca gctcgccacc atgggatgga gctgtatcat cctcttcttg gtactgctgc   1320 tgggcccagcc ggccagtgac cttgaccggt gcaccacttt tgatgatgtt caagctccta   1380
attacactca acatacttca tctatgaggg gggtttacta tcctgatgaa attttttagat   1440 cggacactct ttatttaact caggatttat ttcttccatt ttattctaat gttacagggt   1500
ttcatactat taatcatacg tttggcaacc ctgtcatacc ttttaaggat ggtatttatt   1560
ttgctgccac agagaaatca aatgttgtcc gtggttgggt ttttggttct accatgaaca   1620
acaagtcaca gtcggtgatt attattaaca attctactaa tgttgttata cgagcatgta   1680
```

```
actttgaatt gtgtgacaac cctttctttg ctgtttctaa acccatgggt acacagacac   1740
atactatgat attcgataat gcatttaatt gcactttcga gtacatatct gatgcctttt   1800
cgcttgatgt ttcagaaaag tcaggtaatt ttaaacactt acgagagttt gtgtttaaaa   1860
ataaagatgg gtttctctat gtttataagg gctatcaacc tatagatgta gttcgtgatc   1920
taccttctgg ttttaacact ttgaaaccta ttttttaagtt gcctcttggt attaacatta   1980
caaattttag agccattctt acagcctttt cacctgctca agacatttgg ggcacgtcag   2040
ctgcagccta ttttgttggc tatttaaagc caactacatt tatgctcaag tatgatgaaa   2100
atggtacaat cacagatgct gttgattgtt ctcaaaatcc acttgctgaa ctcaaatgct   2160
ctgttaagag ctttgagatt gacaaaggaa tttaccagac ctctaatttc agggttgttc   2220
cctcaggaga tgttgtgaga ttccctaata ttacaaactt gtgtccttt ggagaggttt   2280
ttaatgctac taaattccct tctgtctatg catgggagag aaaaaaaatt tctaattgtg   2340
ttgctgatta ctctgtgctc tacaactcaa catttttttc aacctttaag tgctatggcg   2400
tttctgccac taagttgaat gatctttgct tctccaatgt ctatgcagat tcttttgtag   2460
tcaagggaga tgatgtaaga caaatagcgc caggacaaac tggtgttatt gctgattata   2520
attataaatt gccagatgat ttcatgggtt gtgtccttgc ttggaatact aggaacattg   2580
atgctacttc aactggtaat tataattata aatataggta tcttagacat ggcaagctta   2640
ggccctttga gagagacata tctaatgtgc ctttctcccc tgatggcaaa ccttgcaccc   2700
cacctgctct taattgttat tggccattaa atgattatgg ttttacacc actactggca   2760
ttggctacca accttacaga gttgtagtac tttcttttga acttttaaat gcaccggcca   2820
cggtttgtgg accaaaatta tccactgacc ttattaagaa ccagtgtgtc aattttaatt   2880
ttaatggact cactggtact ggtgtgttaa ctccttcttc aaagagattt caaccatttc   2940
aacaatttgg ccgtgatgtt tctgatttca ctgattccgt tcgagatcct aaaacatctg   3000
aaatattaga catttcacct tgctctttg ggggtgtaag tgtaattaca cctggaacaa   3060
atgcttcatc tgaagttgct gttctatatc aagatgttaa ctgcactgat gtttctacag   3120
caattcatgc agatcaactc acaccagctt ggcgcatata ttctactgga aacaatgtat   3180
tccagactca ggcaggctgt cttataggag ctgagcatgt cgacacttct tatgagtgcg   3240
acattcctat tggagctggc atttgtgcta gttaccatac agtttcttta ttacgtagta   3300
ctagccaaaa atctattgtg gcttatacta tgtctttagg tgctgatagt tcaattgctt   3360
actctaataa caccattgct atacctacta acttttcaat tagcattact acagaagtaa   3420
tgcctgtttc tatggctaaa acctccgtag attgtaatat gtacatctgc ggagattcta   3480
ctgaatgtgc taatttgctt ctccaatatg gtagcttttg cacacaacta aatcgtgcac   3540
tctcaggtat tgctgctgaa caggatcgca acacacgtga agtgttcgct caagtcaaac   3600
aaatgtacaa accccaact tgaaatatt ttggtggttt taattttca caaatattac   3660
ctgaccctct aaagccaact aagaggtctt ttattgagga cttgctcttt aataaggtga   3720
cactcgctga tgctggcttc atgaagcaat atggcgaatg cctaggtgat attaatgcta   3780
gagatctcat ttgtgcgcag aagttcaatg gacttacagt gttgccacct ctgctcactg   3840
atgatatgat tgctgcctac actgctgctc tagttagtgg tactgccact gctggatgga   3900
catttggtgc tggcgctgct cttcaaatac cttttgctat gcaaatggca tataggttca   3960
atggcattgg agttacccaa aatgttctct atgagaacca aaaacaaatc gccaaccaat   4020
ttaacaaggc gattagtcaa attcaagaat cacttacaac aacatcaact gcattgggca   4080
```

```
agctgcaaga cgttgttaac cagaatgctc aagcattaaa cacacttgtt aaacaactta    4140
gctctaattt tggtgcaatt tcaagtgtgc taaatgatat cctttcgcga cttgataaag    4200
tcgaggcgga ggtacaaatt gacaggttaa ttacaggcag acttcaaagc cttcaaacct    4260
atgtaacaca caactaatc agggctgctg aaatcagggc ttctgctaat cttgctgcta    4320
ctaaaatgtc tgagtgtgtt cttggacaat caaaaagagt tgacttttgt ggaaagggct    4380
accaccttat gtccttccca caagcagccc cgcatggtgt tgtcttccta catgtcacgt    4440
atgtgccatc ccaggagagg aacttcacca cagcgccagc aatttgtcat gaaggcaaag    4500
catacttccc tcgtgaaggt gtttttgtgt ttaatggcac ttcttggttt attacacaga    4560
ggaacttctt ttctccacaa ataattacta cagacaatac atttgtctca ggaaattgtg    4620
atgtcgttat tggcatcatt aacaacacag tttatgatcc tctgcaaccct gagcttgact    4680 cattcaaaga gagctggac aagtacttca aaaatcatac atcaccagat gttgattttg    4740
gcgacatttc aggcattaac gcttctgtcg tcaacattca aaagaaatt gaccgcctca    4800 atgaggtcgc taaaaattta aatgaatcac tcattgacct tcaagaactg gaaaatatg    4860 agcaatatat taaatggcct ctcgacgaac aaaaactcat ctcagaagag gatctgaatg    4920
ctgtgggcca ggacacgcag gaggtcatcg tggtgccaca ctccttgccc tttaaggtgg    4980
tggtgatctc agccatcctg gccctggtgg tgctcaccat catctccctt atcatcctca    5040
tcatgctttg gcagaagaag ccacgttagg cggccgctcg agtgctagca ccaagggccc    5100
cagcgtgttc cccctggccc ccagcagcaa gagcaccagc ggcggcacag ccgccctggg    5160
ctgcctggtg aaggactact tccccgagcc cgtgaccgtg agctggaaca gcggcgcctt    5220
gaccagcggc gtgcacacct tccccgccgt gctgcagagc agcggcctgt acagcctgag    5280
cagcgtggtg accgtgccca gcagcagcct gggcacccag acctacatct gcaacgtgaa    5340
ccacaagccc agcaacacca aggtggacaa acgcgtggag cccaagagct gcgacaagac    5400
ccacacctgc cccccctgcc ctgccccga gctgctgggc ggaccctccg tgttcctgtt    5460
cccccccaag cccaaggaca cactcatgat cagccggacc cccgaggtga cctgcgtggt    5520
ggtggacgtg agccacgagg accccgaggt gaagttcaac tggtacgtgg acggcgtgga    5580
ggtgcacaac gccaagacca gccccgggga ggagcagtac aacagcacct accgggtggt    5640
gagcgtgctc accgtgctgc accaggactg gctgaacggc aaggagtaca agtgcaaggt    5700
gagcaacaag gccctgcctg cccccatcga gaagaccatc agcaaggcca agggccagcc    5760
ccgggagccc caggtgtaca ccctgccccc cagccgggag gagatgacca gaaccaggt    5820 gtccctcacc tgtctggtga agggcttcta ccccagcgac atcgccgtgg agtgggagag    5880
caacggccag cccgagaaca actacaagac caccccccct gtgctggaca cgacggcag    5940 cttcttcctg tacagcaagc tcaccgtgga caagagccgg tggcagcagg caacgtgtt    6000 cagctgcagc gtgatgcacg aggccctgca caaccactac acccagaaga gcctgagcct    6060 gagcccggc aagtgataat ctagagggcc cgtttaaacc cgctgatcag cctcgactgt    6120
gccttctagt tgccagccat ctgttgtttg ccctccccc gtgccttcct tgaccctgga    6180
aggtgccact cccactgtcc tttcctaata aatgaggaa attgcatcgc attgtctgag    6240
taggtgtcat tctattctgg ggggtggggt ggggcaggac agcaagggg aggattggga    6300 agacaatagc aggcatgctg gggatgcggt gggctctatg gcttctgagg cggaaagaac    6360
cagctggggc tctaggggt atccccacgc gccctgtagc ggcgcattaa gcgcggcggg    6420
tgtggtggtt acgcgcagcg tgaccgctac acttgccagc gccctagcgc ccgctccttt    6480
```

```
cgctttcttc ccttcctttc tcgccacgtt cgccggcttt ccccgtcaag ctctaaatcg    6540
ggggctccct ttagggttcc gatttagtgc tttacggcac ctcgacccca aaaaacttga    6600
ttagggtgat ggttcacgta gtgggccatc gccctgatag acggttttc gcccttttgac    6660 gttggagtcc acgttcttta atagtggact cttgttccaa actggaacaa cactcaaccc    6720
tatctcggtc tattcttttg atttataagg gattttgccg atttcggcct attggttaaa    6780
aaatgagctg atttaacaaa aatttaacgc gaattaattc tgtggaatgt gtgtcagtta    6840
gggtgtggaa agtccccagg ctccccagca ggcagaagta tgcaaagcat gcatctcaat    6900
tagtcagcaa ccaggtgtgg aaagtcccca ggctccccag caggcagaag tatgcaaagc    6960
atgcatctca attagtcagc aaccatagtc ccgcccctaa ctccgcccat cccgccccta    7020
actccgccca gttccgccca ttctccgccc catggctgac taattttttt tatttatgca    7080
gaggccgagg ccgcctctgc ctctgagcta ttccagaagt agtgaggagg cttttttgga    7140
ggcctaggct tttgcaaaaa gctcccggga gcttgtatat ccattttcgg atctgatcaa    7200
gagacaggat gaggatcgtt tcgcatgatt gaacaagatg gattgcacgc aggttctccg    7260
gccgcttggg tggagaggct attcggctat gactgggcac aacagacaat cggctgctct    7320
gatgccgccg tgttccggct gtcagcgcag gggcgcccgg ttcttttgt caagaccgac    7380 ctgtccggtg ccctgaatga actgcaggac gaggcagcgc ggctatcgtg gctggccacg    7440
acgggcgttc cttgcgcagc tgtgctcgac gttgtcactg aagcgggaag gactggctg    7500 ctattgggcg aagtgccggg gcaggatctc ctgtcatctc accttgctcc tgccgagaaa    7560
gtatccatca tggctgatgc aatgcggcgg ctgcatacgc ttgatccggc tacctgccca    7620
ttcgaccacc aagcgaaaca tcgcatcgag cgagcacgta ctcggatgga agccggtctt    7680
gtcgatcagg atgatctgga cgaagagcat caggggctcg cgccagccga actgttcgcc    7740
aggctcaagg cgcgcatgcc cgacggcgag gatctcgtcg tgacccatgg cgatgcctgc    7800
ttgccgaata tcatggtgga aaatggccgc ttttctggat tcatcgactg tggccggctg    7860
ggtgtggcgg accgctatca ggacatagcg ttggctaccc gtgatattgc tgaagagctt    7920
ggcggcgaat gggctgaccg cttcctcgtg ctttacggta tcgccgctcc cgattcgcag    7980
cgcatcgcct tctatcgcct tcttgacgag ttcttctgag cgggactctg gggttcgaaa    8040
tgaccgacca agcgacgccc aacctgccat cacgagattt cgattccacc gccgccttct    8100
atgaaaggtt gggcttcgga atcgttttcc gggacgccgg ctggatgatc ctccagcgcg    8160
gggatctcat gctggagttc ttcgcccacc ccaacttgtt tattgcagct tataatggtt    8220
acaaataaag caatagcatc acaaatttca caaataaagc atttttttca ctgcattcta    8280
gttgtggttt gtccaaactc atcaatgtat cttatcatgt ctgtataccg tcgacctcta    8340
gctagagctt ggcgtaatca tggtcatagc tgtttcctgt gtgaaattgt tatccgctca    8400
caattccaca acacatacga gccggaagca taaagtgtaa agcctggggt gcctaatgag    8460
tgagctaact cacattaatt gcgttgcgct cactgcccgc tttccagtcg ggaaacctgt    8520
cgtgccagct gcattaatga atcggccaac gcgcggggag aggcggtttg cgtattgggc    8580
gctcttccgc ttcctcgctc actgactcgc tgcgctcggt cgttcggctg cggcgagcgg    8640
tatcagctca ctcaaaggcg gtaatacggt tatccacaga atcaggggat aacgcaggaa    8700
agaacatgtg agcaaaaggc cagcaaaagg ccaggaaccg taaaaaggcc gcgttgctgg    8760
cgttttccca taggctccgc cccctgacg agcatcacaa aaatcgacgc tcaagtcaga    8820
ggtggcgaaa cccgacagga ctataaagat accaggcgtt tcccctgga agctccctcg    8880
```

| | | | | |
|---|---|---|---|---|
| tgcgctctcc | tgttccgacc | ctgccgctta | ccggatacct | gtccgccttt | ctcccttcgg | 8940 |
| gaagcgtggc | gctttctcat | agctcacgct | gtaggtatct | cagttcggtg | taggtcgttc | 9000 |
| gctccaagct | gggctgtgtg | cacgaacccc | ccgttcagcc | cgaccgctgc | gccttatccg | 9060 |
| gtaactatcg | tcttgagtcc | aacccggtaa | gacacgactt | atcgccactg | gcagcagcca | 9120 |
| ctggtaacag | gattagcaga | gcgaggtatg | taggcggtgc | tacagagttc | ttgaagtggt | 9180 |
| ggcctaacta | cggctacact | agaagaacag | tatttggtat | ctgcgctctg | ctgaagccag | 9240 |
| ttaccttcgg | aaaaagagtt | ggtagctctt | gatccggcaa | acaaaccacc | gctggtagcg | 9300 |
| gtttttttgt | ttgcaagcag | cagattacgc | gcagaaaaaa | aggatctcaa | gaagatcctt | 9360 |
| tgatcttttc | tacggggtct | gacgctcagt | ggaacgaaaa | ctcacgttaa | gggattttgg | 9420 |
| tcatgagatt | atcaaaaagg | atcttcacct | agatccttt | aaattaaaaa | tgaagtttta | 9480 |
| aatcaatcta | aagtatatat | gagtaaactt | ggtctgacag | ttaccaatgc | ttaatcagtg | 9540 |
| aggcacctat | ctcagcgatc | tgtctatttc | gttcatccat | agttgcctga | ctccccgtcg | 9600 |
| tgtagataac | tacgatacgg | gagggcttac | catctggccc | cagtgctgca | atgataccgc | 9660 |
| gagacccacg | ctcaccggct | ccagatttat | cagcaataaa | ccagccagcc | ggaagggccg | 9720 |
| agcgcagaag | tggtcctgca | actttatccg | cctccatcca | gtctattaat | tgttgccggg | 9780 |
| aagctagagt | aagtagttcg | ccagttaata | gtttgcgcaa | cgttgttgcc | attgctacag | 9840 |
| gcatcgtggt | gtcacgctcg | tcgtttggta | tggcttcatt | cagctccggt | tcccaacgat | 9900 |
| caaggcgagt | tacatgatcc | cccatgttgt | gcaaaaaagc | ggttagctcc | ttcggtcctc | 9960 |
| cgatcgttgt | cagaagtaag | ttggccgcag | tgttatcact | catggttatg | gcagcactgc | 10020 |
| ataattctct | tactgtcatg | ccatccgtaa | gatgcttttc | tgtgactggt | gagtactcaa | 10080 |
| ccaagtcatt | ctgagaatag | tgtatgcggc | gaccgagttg | ctcttgcccg | gcgtcaatac | 10140 |
| gggataatac | cgcgccacat | agcagaactt | taaaagtgct | catcattgga | aaacgttctt | 10200 |
| cggggcgaaa | actctcaagg | atcttaccgc | tgttgagatc | cagttcgatg | taacccactc | 10260 |
| gtgcacccaa | ctgatcttca | gcatctttta | ctttcaccag | cgtttctggg | tgagcaaaaa | 10320 |
| caggaaggca | aaatgccgca | aaaaagggaa | taagggcgac | acggaaatgt | tgaatactca | 10380 |
| tactcttcct | ttttcaatat | tattgaagca | tttatcaggg | ttattgtctc | atgagcggat | 10440 |
| acatatttga | atgtatttag | aaaaataaac | aaataggggt | tccgcgcaca | tttccccgaa | 10500 |
| aagtgccacc | tgacg | | | | | 10515 |

<210> SEQ ID NO 85
<211> LENGTH: 8777
<212> TYPE: DNA
<213> ORGANISM: Artificial sequence
<220> FEATURE:
<223> OTHER INFORMATION: pIg-C909-Ckappa
<220> FEATURE:
<221> NAME/KEY: misc_feature
<222> LOCATION: (1328)..(3860)
<223> OTHER INFORMATION: Stuffer

<400> SEQUENCE: 85

| | | | | |
|---|---|---|---|---|
| tcgacggatc | gggagatctc | ccgatcccct | atggtgcact | ctcagtacaa | tctgctctga | 60 |
| tgccgcatag | ttaagccagt | atctgctccc | tgcttgtgtg | ttggaggtcg | ctgagtagtg | 120 |
| cgcgagcaaa | atttaagcta | caacaaggca | aggcttgacc | gacaattgtt | aattaacatg | 180 |
| aagaatctgc | ttagggttag | gcgttttgcg | ctgcttcgct | aggtggtcaa | tattggccat | 240 |
| tagccatatt | attcattggt | tatatagcat | aaatcaatat | tggctattgg | ccattgcata | 300 |

```
cgttgtatcc atatcataat atgtacattt atattggctc atgtccaaca ttaccgccat    360
gttgacattg attattgact agttattaat agtaatcaat tacggggtca ttagttcata    420
gcccatatat ggagttccgc gttacataac ttacggtaaa tggcccgcct ggctgaccgc    480
ccaacgaccc ccgcccattg acgtcaataa tgacgtatgt tcccatagta acgccaatag    540
ggactttcca ttgacgtcaa tgggtggagt atttacggta aactgcccac ttggcagtac    600
atcaagtgta tcatatgcca agtacgcccc ctattgacgt caatgacggt aaatggcccg    660
cctggcatta tgcccagtac atgaccttat gggactttcc tacttggcag tacatctacg    720
tattagtcat cgctattacc atggtgatgc ggttttggca gtacatcaat gggcgtggat    780
agcggtttga ctcacgggga tttccaagtc tccaccccat tgacgtcaat gggagtttgt    840
tttggcacca aaatcaacgg gactttccaa aatgtcgtaa caactccgcc ccattgacgc    900
aaatgggcgg taggcgtgta cggtgggagg tctatataag cagagctcgt ttagtgaacc    960
gtcagatcgc ctggagacgc catccacgct gttttgacct ccatagaaga caccgggacc   1020
gatccagcct ccgcggccgg gaacggtgca ttggaatcga tgactctctt aggtagcctt   1080
gcagaagttg gtcgtgaggc actgggcagg taagtatcaa ggttacaaga caggtttaag   1140
gagatcaata gaaactgggc ttgtcgagac agagaagact cttgcgtttc tgataggcac   1200
ctattggtct tactgacatc cactttgcct ttctctccac aggtgtccac tcccagttca   1260
attacagctc gccaccatgc ggctgcccgc ccagctgctg gccttctca tgctgtgggt    1320 gcccgcctcg agatctatcg atgcatgcca tggtaccaag cttgccacca tgagcagcag   1380
ctcttggctg ctgctgagcc tggtggccgt gacagccgcc cagagcacca tcgaggagca   1440
ggccaagacc ttcctggaca gttcaacca cgaggccgag gacctgttct accagagcag   1500
cctggccagc tggaactaca acaccaacat caccgaggag aacgtgcaga acatgaacaa   1560
cgccggcgac aagtggagcg ccttcctgaa ggagcagagc acactggccc agatgtaccc   1620
cctgcaggag atccagaacc tgaccgtgaa gctgcagctg caggccctgc agcagaacgg   1680
cagcagcgtg ctgagcgagg acaagagcaa gcggctgaac accatcctga acaccatgtc   1740
caccatctac agcaccggca aagtgtgcaa ccccgacaac ccccaggagt gcctgctgct   1800
ggagcccggc ctgaacgaga tcatggccaa cagcctggac tacaacgagc ggctgtgggc   1860
ctgggagagc tggcggagcg aagtgggcaa gcagctgcgg cccctgtacg aggagtacgt   1920
ggtgctgaag aacgagatgg ccagggccaa ccactacgag gactacgcg actactggag    1980 aggcgactac gaagtgaacg gcgtggacgg ctacgactac agcagaggcc agctgatcga   2040
ggacgtggag cacaccttcg aggagatcaa gcctctgtac gagcacctgc acgcctacgt   2100
gcgggccaag ctgatgaacg cctaccccag ctacatcagc cccatcggct gcctgcccgc   2160
ccacctgctg ggcgacatgt ggggccggtt ctggaccaac ctgtacagcc tgaccgtgcc   2220
cttcggccag aagcccaaca tcgacgtgac cgacgccatg gtggaccagg cctgggacgc   2280
ccagcggatc ttcaaggagg ccgagaagtt cttcgtgagc gtgggcctgc caacatgac    2340 ccagggcttt gggagaaca gcatgctgac cgaccccggc aatgtgcaga aggccgtgtg    2400 ccacccacc gcctgggacc tgggcaaggg cgacttccgg atcctgatgt gcaccaaagt    2460
gaccatggac gacttcctga ccgcccacca cgagatgggc cacatccagt acgacatggc   2520
ctacgccgcc cagcccttcc tgctgcggaa cggcgccaac gagggctttc acgaggccgt   2580
gggcgagatc atgagcctga cgccgccac ccccaagcac ctgaagagca tcggcctgct    2640
gagccccgac ttccaggagg acaacgagac cgagatcaac ttcctgctga gcaggccct    2700
```

-continued

```
gaccatcgtg ggcaccctgc ccttcaccta catgctggag aagtggcggt ggatggtgtt 2760
taagggcgag atccccaagg accagtggat gaagaagtgg tgggagatga agcgggagat 2820
cgtgggcgtg gtggagcccg tgccccacga cgagacctac tgcgaccccg ccagcctgtt 2880
```

```

ccacgtgagc aacgactact ccttcatccg gtactacacc cggaccctgt accagttcca 2940
gttccaggag gccctgtgcc aggccgccaa gcacgagggc cccctgcaca agtgcgacat 3000
cagcaacagc accgaggccg gacagaaact gttcaacatg ctgcggctgg gcaagagcga 3060
gccctggacc ctggccctgg agaatgtggt gggcgccaag aacatgaatg tgcgccccct 3120
gctgaactac ttcgagcccc tgttcacctg gctgaaggac cagaacaaga acagcttcgt 3180
gggctggagc accgactgga gccccctacgc cgaccagagc atcaaagtgc ggatcagcct 3240
gaagagcgcc ctgggcgaca aggcctacga gtggaacgac aacgagatgt acctgttccg 3300
gagcagcgtg gcctatgcca tgcggcagta cttcctgaaa gtgaagaacc agatgatcct 3360
gttcggcgag gaggacgtga gagtggccaa cctgaagccc cggatcagct tcaacttctt 3420
cgtgaccgcc cccaagaacg tgagcgacat catcccccgg accgaagtgg agaaggccat 3480
ccggatgagc cggagccgga tcaacgacgc cttccggctg aacgacaact ccctggagtt 3540
cctgggcatc cagcccaccc tgggccctcc caaccagccc cccgtgagca tctggctgat 3600
cgtgtttggc gtggtgatgg gcgtgatcgt ggtgggaatc gtgatcctga tcttcaccgg 3660
catccgggac cggaagaaga agaacaaggc ccggagcggc gagaacccct acgccagcat 3720
cgatatcagc aagggcgaga acaaccccgg cttccagaac accgacgacg tgcagaccag 3780
```

```

cttctgataa tctagaacga gctcgaattc gaagcttctg cagacgcgtc gacgtcatat 3840
ggatccgata tcgccgtggc ggccgcaccc agcgtgttca tcttcccccc ctccgacgag 3900
cagctgaaga gcggcaccgc cagcgtggtg tgcctgctga acaacttcta cccccgggag 3960
gccaaggtgc agtggaaggt ggacaacgcc ctgcagagcg gcaacagcca ggagagcgtg 4020
accgagcagg acagcaagga ctccacctac agcctgagca gcaccctcac cctgagcaag 4080
gccgactacg agaagcacaa ggtgtacgcc tgcgaggtga cccaccaggg cctgagcagc 4140
cccgtgacca agagcttcaa ccggggcgag tgttaataga cttaagttta aaccgctgat 4200
cagcctcgac tgtgccttct agttgccagc catctgttgt ttgcccctcc cccgtgcctt 4260
ccttgaccct ggaaggtgcc actcccactg tcctttccta ataaaatgag gaaattgcat 4320
cgcattgtct gagtaggtgt cattctattc tggggggtgg ggtggggcag gacagcaagg 4380
gggaggattg ggaagacaat agcaggcatg ctggggatgc ggtgggctct atggcttctg 4440
aggcggaaag aaccagctgg ggctctaggg ggtatcccca cgcgccctgt agcggcgcat 4500
taagcgcggc gggtgtggtg gttacgcgca gcgtgaccgc tacacttgcc agcgccctag 4560
cgcccgctcc tttcgctttc ttcccttcct ttctcgccac gttcgccggc tttccccgtc 4620
aagctctaaa tcgggggctc cctttagggt tccgatttag tgctttacgg cacctcgacc 4680
ccaaaaaact tgattagggt gatggttcac gtagtgggcc atcgccctga tagacggttt 4740
ttcgcccttt gacgttggag tccacgttct ttaatagtgg actcttgttc caaactggaa 4800
caacactcaa ccctatctcg gtctattctt ttgatttata agggattttg gccatttcgg 4860
cctattggtt aaaaaatgag ctgatttaac aaaaatttaa cgcgaattaa ttctgtggaa 4920
tgtgtgtcag ttagggtgtg gaaagtcccc aggctcccca gcaggcagaa gtatgcaaag 4980
catgcatctc aattagtcag caaccaggtg tggaaagtcc ccaggctccc cagcaggcag 5040
aagtatgcaa agcatgcatc tcaattagtc agcaaccata gtcccgcccc taactccgcc 5100
```

```
catcccgccc ctaactccgc ccagttccgc ccattctccg ccccatggct gactaatttt    5160
ttttatttat gcagaggccg aggccgcctc tgcctctgag ctattccaga agtagtgagg    5220 aggcttttt ggaggcctag cttttgcaa aaagctcccg ggagcttgta tatccatttt     5280
cggatctgat cagcacgtga tgaaaaagcc tgaactcacc gcgacgtctg tcgagaagtt    5340
tctgatcgaa aagttcgaca gcgtctccga cctgatgcag ctctcggagg gcgaagaatc    5400
tcgtgctttc agcttcgatg taggagggcg tggatatgtc ctgcgggtaa atagctgcgc    5460
cgatggtttc tacaaagatc gttatgttta tcggcacttt gcatcggccg cgctcccgat    5520
tccggaagtg cttgacattg ggaattcag cgagagcctg acctattgca tctcccgccg     5580
tgcacagggt gtcacgttgc aagacctgcc tgaaaccgaa ctgcccgctg ttctgcagcc    5640
ggtcgcggag gccatggatg cgatcgctgc ggccgatctt agccagacga gcgggttcgg    5700
cccattcgga ccacaaggaa tcggtcaata cactacatgg cgtgatttca tatgcgcgat    5760
tgctgatccc catgtgtatc actggcaaac tgtgatggac gacaccgtca gtgcgtccgt    5820
cgcgcaggct ctcgatgagc tgatgctttg ggccgaggac tgccccgaag tccggcacct    5880
cgtgcacgcg gatttcggct ccaacaatgt cctgacggac aatggccgca taacagcggt    5940
cattgactgg agcgaggcga tgttcgggga ttcccaatac gaggtcgcca acatcttctt    6000
ctggaggccg tggttggctt gtatggagca gcagacgcgc tacttcgagc ggaggcatcc    6060
ggagcttgca ggatcgccgc ggctccgggc gtatatgctc cgcattggtc ttgaccaact    6120
ctatcagagc ttggttgacg gcaatttcga tgatgcagct tgggcgcagg tcgatgcga    6180 cgcaatcgtc cgatccggag ccgggactgt cgggcgtaca caaatcgccc gcagaagcgc    6240
ggccgtctgg accgatggct gtgtagaagt actcgccgat agtggaaacc gacgccccag    6300
cactcgtccg agggcaaagg aatagcacgt gctacgagat ttcgattcca ccgccgcctt    6360
ctatgaaagg ttgggcttcg gaatcgtttt ccgggacgcc ggctggatga tcctccagcg    6420
cggggatctc atgctggagt tcttcgccca ccccaacttg tttattgcag cttataatgg    6480
ttacaaataa agcaatagca tcacaaattt cacaaataaa gcattttttt cactgcattc    6540
tagttgtggt ttgtccaaac tcatcaatgt atcttatcat gtctgtatac cgtcgacctc    6600
tagctagagc ttggcgtaat catggtcata gctgtttcct gtgtgaaatt gttatccgct    6660
cacaattcca cacaacatac gagccggaag cataaagtgt aaagcctggg gtgcctaatg    6720
agtgagctaa ctcacattaa ttgcgttgcg ctcactgccc gctttccagt cgggaaacct    6780
gtcgtgccag ctgcattaat gaatcggcca acgcgcgggg agaggcggtt tgcgtattgg    6840
gcgctcttcc gcttcctcgc tcactgactc gctgcgctcg tcgttcggc tgcggcgagc      6900 ggtatcagct cactcaaagg cggtaatacg gttatccaca gaatcagggg ataacgcagg    6960
aaagaacatg tgagcaaaag gccagcaaaa ggccaggaac cgtaaaaagg ccgcgttgct    7020
ggcgtttttc cataggctcc gcccccctga cgagcatcac aaaaatcgac gctcaagtca    7080
gaggtggcga aacccgacag gactataaag ataccaggcg tttccccctg gaagctccct    7140
cgtgcgctct cctgttccga ccctgccgct taccggatac ctgtccgcct ttctcccttc    7200
gggaagcgtg cgctttctc atagctcacg ctgtaggtat ctcagttcgg tgtaggtcgt     7260
tcgctccaag ctgggctgtg tgcacgaacc ccccgttcag cccgaccgct gcgccttatc    7320
cggtaactat cgtcttgagt ccaacccggt aagacacgac ttatcgccac tggcagcagc    7380
cactggtaac aggattagca gagcgaggta tgtaggcggt gctacagagt tcttgaagtg    7440
gtggcctaac tacggctaca ctagaagaac agtatttggt atctgcgctc tgctgaagcc    7500
```

```
agttaccttc ggaaaaagag ttggtagctc ttgatccggc aaacaaacca ccgctggtag    7560
cggttttttt gtttgcaagc agcagattac gcgcagaaaa aaaggatctc aagaagatcc    7620
tttgatcttt tctacggggt ctgacgctca gtggaacgaa aactcacgtt aagggatttt    7680
ggtcatgaga ttatcaaaaa ggatcttcac ctagatcctt ttaaattaaa aatgaagttt    7740
taaatcaatc taaagtatat atgagtaaac ttggtctgac agttaccaat gcttaatcag    7800
tgaggcacct atctcagcga tctgtctatt tcgttcatcc atagttgcct gactccccgt    7860
cgtgtagata actacgatac gggagggctt accatctggc cccagtgctg caatgatacc    7920
gcgagaccca cgctcaccgg ctccagattt atcagcaata accagccag ccggaagggc    7980 cgagcgcaga gtggtcctg caactttatc cgcctccatc cagtctatta attgttgccg    8040
ggaagctaga gtaagtagtt cgccagttaa tagtttgcgc aacgttgttg ccattgctac    8100
aggcatcgtg gtgtcacgct cgtcgtttgg tatggcttca ttcagctccg gttcccaacg    8160
atcaaggcga gttacatgat cccccatgtt gtgcaaaaaa gcggttagct ccttcggtcc    8220
tccgatcgtt gtcagaagta agttggccgc agtgttatca ctcatggtta tggcagcact    8280
gcataattct cttactgtca tgccatccgt aagatgcttt tctgtgactg gtgagtactc    8340
aaccaagtca ttctgagaat agtgtatgcg gcgaccgagt tgctcttgcc cggcgtcaat    8400
acgggataat accgcgccac atagcagaac tttaaaagtg ctcatcattg gaaaacgttc    8460
ttcggggcga aaactctcaa ggatcttacc gctgttgaga tccagttcga tgtaacccac    8520
tcgtgcaccc aactgatctt cagcatcttt tactttcacc agcgtttctg gtgagcaaa    8580 aacaggaagg caaaatgccg caaaaaaggg aataagggcg acacggaaat gttgaatact    8640
catactcttc ctttttcaat attattgaag catttatcag ggttattgtc tcatgagcgg    8700
atacatattt gaatgtattt agaaaaataa acaaataggg gttccgcgca catttccccg    8760
aaaagtgcca cctgacg                                                  8777

<210> SEQ ID NO 86
<211> LENGTH: 8792
<212> TYPE: DNA
<213> ORGANISM: Artificial sequence
<220> FEATURE:
<223> OTHER INFORMATION: Vector pIg-C910-Clambda
<220> FEATURE:
<221> NAME/KEY: misc_feature
<222> LOCATION: (1330)..(3869)
<223> OTHER INFORMATION: Stuffer

<400> SEQUENCE: 86
tcgacggatc gggagatctc ccgatcccct atggtgcact ctcagtacaa tctgctctga      60
tgccgcatag ttaagccagt atctgctccc tgcttgtgtg ttggaggtcg ctgagtagtg     120
cgcgagcaaa atttaagcta caacaaggca aggcttgacc gacaattgtt aattaacatg     180
aagaatctgc ttagggttag gcgttttgcg ctgcttcgct aggtggtcaa tattggccat     240
tagccatatt attcattggt tatatagcat aaatcaatat ggctattgg ccattgcata     300 cgttgtatcc atatcataat atgtacattt atattggctc atgtccaaca ttaccgccat     360
gttgacattg attattgact agttattaat agtaatcaat tacggggtca ttagttcata     420
gcccatatat ggagttccgc gttacataac ttacggtaaa tggcccgcct ggctgaccgc     480
ccaacgaccc cgcccattg acgtcaataa tgacgtatgt tcccatagta acgccaatag     540
ggactttcca ttgacgtcaa tgggtggagt atttacggta aactgcccac ttggcagtac     600
atcaagtgta tcatatgcca agtacgcccc ctattgacgt caatgacggt aaatggcccg     660
```

```
cctggcatta tgcccagtac atgacccttat gggactttcc tacttggcag tacatctacg    720
tattagtcat cgctattacc atggtgatgc ggttttggca gtacatcaat gggcgtggat    780
agcggtttga ctcacgggga tttccaagtc tccaccccat tgacgtcaat gggagtttgt    840
tttggcacca aaatcaacgg gactttccaa aatgtcgtaa caactccgcc ccattgacgc    900
aaatgggcgg taggcgtgta cggtgggagg tctatataag cagagctcgt ttagtgaacc    960
gtcagatcgc ctggagacgc catccacgct gttttgacct ccatagaaga caccgggacc   1020
gatccagcct ccgcggccgg aacggtgca ttggaatcga tgactctctt aggtagcctt   1080
gcagaagttg gtcgtgaggc actgggcagg taagtatcaa ggttacaaga caggtttaag   1140
gagatcaata gaaactgggc ttgtcgagac agagaagact cttgcgtttc tgataggcac   1200
ctattggtct tactgacatc cactttgcct ttctctccac aggtgtccac tcccagttca   1260
attacagctc gccaccatgc ggttctccgc tcagctgctg ggccttctgg tgctgtggat   1320
tcccggcgtc tcgagatcta tcgatgcatg ccatggtacc aagcttgcca ccatgagcag   1380
cagctcttgg ctgctgctga gcctggtggc cgtgacagcc gcccagagca ccatcgagga   1440
gcaggccaag accttcctgg acaagttcaa ccacgaggcc gaggacctgt tctaccagag   1500
cagcctggcc agctggaact acaacaccaa catcaccgag gagaacgtgc agaacatgaa   1560
caacgccggc gacaagtgga gcgccttcct gaaggagcag agcacactgg cccagatgta   1620 cccctgcag gagatccaga acctgaccgt gaagctgcag ctgcaggccc tgcagcagaa   1680
cggcagcagc gtgctgagcg aggacaagag caagcggctg aacaccatcc tgaacaccat   1740
gtccaccatc tacagcaccg gcaaagtgtg caaccccgac aaccccagg agtgcctgct   1800 gctggagccc ggcctgaacg agatcatggc caacagcctg gactacaacg agcggctgtg   1860
ggcctgggag agctggcgga gcgaagtggg caagcagctg cggcccctgt acgaggagta   1920
cgtggtgctg aagaacgaga tggccaggc caaccactac gaggactacg gcgactactg   1980
gagaggcgac tacgaagtga acggcgtgga cggctacgac tacagcagag gccagctgat   2040
cgaggacgtg gagcacacct tcgaggagat caagcctctg tacgagcacc tgcacgccta   2100
cgtgcgggcc aagctgatga acgcctaccc cagctacatc agccccatcg gctgcctgcc   2160
cgcccacctg ctgggcgaca tgtgggcccg gttctggacc aacctgtaca gcctgaccgt   2220
gcccttcggc cagaagccca acatcgacgt gaccgacgcc atggtggacc aggcctggga   2280
cgcccagcgg atcttcaagg aggccgagaa gttcttcgtg agcgtgggcc tgcccaacat   2340
gacccagggc ttttgggaga acagcatgct gaccgacccc ggcaatgtgc agaaggccgt   2400
gtgccacccc accgcctggg acctgggcaa gggcgacttc cggatcctga tgtgcaccaa   2460
agtgaccatg gacgacttcc tgaccgccca ccacgagatg ggccacatcc agtacgacat   2520
ggcctacgcc gcccagccct tcctgctgcg gaacggcgcc aacgagggct tcacgaggc   2580 cgtgggcgag atcatgagcc tgagcgccgc caccccaag cacctgaaga gcatcggcct   2640
gctgagcccc gacttccagg aggacaacga gaccgagatc aacttcctgc tgaagcaggc   2700
cctgaccatc gtgggcaccc tgcccttcac ctacatgctg gagaagtggc ggtggatggt   2760
gtttaagggc gagatcccca aggaccagtg gatgaagaag tggtgggaga tgaagcggga   2820
gatcgtgggc gtggtggagc ccgtgcccca cgacgagacc tactgcgacc ccgccagcct   2880
gttccacgtg agcaacgact actccttcat ccggtactac acccggaccc tgtaccagtt   2940
ccagttccag gaggccctgt gccaggccgc caagcacgag ggcccctgc acaagtgcga   3000 catcagcaac agcaccgagg ccggacagaa actgttcaac atgctgcggc tgggcaagag   3060
```

```
cgagccctgg accctggccc tggagaatgt ggtgggcgcc aagaacatga atgtgcgccc   3120
cctgctgaac tacttcgagc ccctgttcac ctggctgaag gaccagaaca agaacagctt   3180
cgtgggctgg agcaccgact ggagccccta cgccgaccag agcatcaaag tgcggatcag   3240
cctgaagagc gccctgggcg acaaggccta cgagtggaac gacaacgaga tgtacctgtt   3300
ccggagcagc gtggcctatg ccatgcggca gtacttcctg aaagtgaaga accagatgat   3360
cctgttcggc gaggaggacg tgagagtggc caacctgaag ccccggatca gcttcaactt   3420
cttcgtgacc gcccccaaga acgtgagcga catcatcccc cggaccgaag tggagaaggc   3480
catccggatg agccggagcc ggatcaacga cgccttccgg ctgaacgaca actccctgga   3540
gttcctgggc atccagccca ccctgggccc tccaaccag ccccccgtga gcatctggct   3600
gatcgtgttt ggcgtggtga tgggcgtgat cgtggtggga atcgtgatcc tgatcttcac   3660
cggcatccgg gaccgaaaga agaagaacaa ggcccggagc ggcgagaacc cctacgccag   3720
catcgatatc agcaagggcg agaacaaccc cggcttccag aacaccgacg acgtgcagac   3780
cagcttctga taatctagaa cgagctcgaa ttcgaagctt ctgcagacgc gtcgacgtca   3840
tatggatccg atatcgccgt ggcggccgca ggccagccca aggccgctcc cagcgtgacc   3900
ctgttccccc cctcctccga ggagctgcag gccaacaagg ccaccctggt gtgcctcatc   3960
agcgacttct accctggcgc cgtgaccgtg gcctggaagg ccgacagcag ccccgtgaag   4020
gccggcgtgg agaccaccac ccccagcaag cagagcaaca acaagtacgc cgccagcagc   4080
tacctgagcc tcaccccga gcagtggaag agccaccgga gctacagctg ccaggtgacc   4140
cacgagggca gcaccgtgga gaagaccgtg gcccccaccg agtgcagcta atagacttaa   4200
gtttaaaccg ctgatcagcc tcgactgtgc cttctagttg ccagccatct gttgtttgcc   4260
cctcccccgt gccttccttg accctggaag gtgccactcc cactgtcctt tcctaataaa   4320
atgaggaaat tgcatcgcat tgtctgagta ggtgtcattc tattctgggg ggtggggtgg   4380
ggcaggacag caagggggag gattgggaag acaatagcag gcatgctggg gatgcggtgg   4440
gctctatggc ttctgaggcg gaaagaacca gctggggctc tagggggtat ccccacgcgc   4500
cctgtagcgg cgcattaagc gcggcgggtg tggtggttac gcgcagcgtg accgctacac   4560
ttgccagcgc cctagcgccc gctcctttcg ctttcttccc ttcctttctc gccacgttcg   4620
ccggctttcc ccgtcaagct ctaaatcggg ggctcccttt agggttccga tttagtgctt   4680
tacggcacct cgaccccaaa aaacttgatt agggtgatgg ttcacgtagt gggccatcgc   4740
cctgatagac ggttttcgc cctttgacgt tggagtccac gttctttaat agtggactct   4800
tgttccaaac tggaacaaca ctcaacccta tctcggtcta ttcttttgat ttataaggga   4860
ttttggccat tcggcctat tggttaaaaa atgagctgat ttaacaaaaa tttaacgcga   4920
attaattctg tggaatgtgt gtcagttagg gtgtggaaag tccccaggct ccccagcagg   4980
cagaagtatg caaagcatgc atctcaatta gtcagcaacc aggtgtggaa agtccccagg   5040
ctccccagca ggcagaagta tgcaaagcat gcatctcaat tagtcagcaa ccatagtccc   5100
gcccctaact ccgcccatcc cgcccctaac tccgcccagt tccgcccatt ctccgcccca   5160
tggctgacta attttttta tttatgcaga ggccgaggcc gcctctgcct ctgagctatt   5220
ccagaagtag tgaggaggct ttttggagg cctaggcttt tgcaaaaagc tcccgggagc   5280
ttgtatatcc attttcggat ctgatcagca cgtgatgaaa aagcctgaac tcaccgcgac   5340
gtctgtcgag aagtttctga tcgaaaagtt cgacagcgtc tccgacctga tgcagctctc   5400
ggagggcgaa gaatctcgtg ctttcagctt cgatgtagga gggcgtggat atgtcctgcg   5460
```

```
ggtaaatagc tgcgccgatg gtttctacaa agatcgttat gtttatcggc actttgcatc   5520
ggccgcgctc ccgattccgg aagtgcttga cattgggaa ttcagcgaga gcctgaccta    5580
ttgcatctcc cgccgtgcac agggtgtcac gttgcaagac ctgcctgaaa ccgaactgcc   5640
cgctgttctg cagccggtcg cggaggccat ggatgcgatc gctgcggccg atcttagcca   5700
gacgagcggg ttcggcccat tcggaccgca aggaatcggt caatacacta catggcgtga   5760
tttcatatgc gcgattgctg atccccatgt gtatcactgg caaactgtga tggacgacac   5820
cgtcagtgcg tccgtcgcgc aggctctcga tgagctgatg ctttgggccg aggactgccc   5880
cgaagtccgg cacctcgtgc acgcggattt cggctccaac aatgtcctga cggacaatgg   5940
ccgcataaca gcggtcattg actggagcga ggcgatgttc ggggattccc aatacgaggt   6000
cgccaacatc ttcttctgga ggccgtggtt ggcttgtatg gagcagcaga cgcgctactt   6060
cgagcggagg catccggagc ttgcaggatc gccgcggctc cggcgtata tgctccgcat    6120 tggtcttgac caactctatc agagcttggt tgacggcaat tcgatgatg cagcttgggc    6180 gcagggtcga tgcgacgcaa tcgtccgatc cggagccggg actgtcgggc gtacacaaat   6240
cgcccgcaga agcgcggccg tctggaccga tggctgtgta aagtactcg ccatagtgg     6300 aaaccgacgc cccagcactc gtccgagggc aaggaatag cacgtgctac gagatttcga    6360
ttccaccgcc gccttctatg aaaggttggg cttcggaatc gttttccggg acgccggctg   6420
gatgatcctc cagcgcgggg atctcatgct ggagttcttc gcccaccca acttgtttat    6480 tgcagcttat aatggttaca aataaagcaa tagcatcaca aatttcacaa ataaagcatt   6540
tttttcactg cattctagtt gtggtttgtc caaactcatc aatgtatctt atcatgtctg   6600
tataccgtcg acctctagct agagcttggc gtaatcatgg tcatagctgt ttcctgtgtg   6660
aaattgttat ccgctcacaa ttccacacaa catacgagcc ggaagcataa agtgtaaagc   6720
ctggggtgcc taatgagtga gctaactcac attaattgcg ttgcgctcac tgcccgcttt   6780
ccagtcggga aacctgtcgt gccagctgca ttaatgaatc ggccaacgcg cggggagagg   6840
cggtttgcgt attgggcgct cttccgcttc ctcgctcact gactcgctgc gctcggtcgt   6900
tcggctgcgg cgagcggtat cagctcactc aaaggcggta atacggttat ccacagaatc   6960 agggataac gcaggaaaga acatgtgagc aaaaggccag caaaaggcca ggaaccgtaa     7020
aaaggccgcg ttgctggcgt ttttccatag gctccgcccc cctgacgagc atcacaaaaa   7080
tcgacgctca agtcagaggt ggcgaaaccc gacaggacta taaagatacc aggcgtttcc   7140
ccctggaagc tccctcgtgc gctctcctgt tccgaccctg ccgcttaccg gatacctgtc   7200
cgcctttctc ccttcgggaa gcgtggcgct ttctcatagc tcacgctgta ggtatctcag   7260
ttcggtgtag tcgttcgct ccaagctggg ctgtgtgcac gaaccccccg ttcagcccga    7320
ccgctgcgcc ttatccggta actatcgtct tgagtccaac ccggtaagac acgacttatc   7380
gccactggca gcagccactg gtaacaggat tagcagagcg aggtatgtag gcggtgctac   7440
agagttcttg aagtggtggc ctaactacgg ctacactaga agaacagtat ttggtatctg   7500
cgctctgctg aagccagtta ccttcggaaa aagagttggt agctcttgat ccggcaaaca   7560
aaccaccgct ggtagcggtt ttttgtttg caagcagcag attacgcgca gaaaaaaagg    7620
atctcaagaa gatcctttga tcttttctac ggggtctgac gctcagtgga acgaaaactc   7680
acgttaaggg attttggtca tgagattatc aaaaaggatc ttcacctaga tccttttaaa   7740
ttaaaaatga agttttaaat caatctaaag tatatatgag taaacttggt ctgacagtta   7800
ccaatgctta atcagtgagg cacctatctc agcgatctgt ctatttcgtt catccatagt   7860
```

```
tgcctgactc cccgtcgtgt agataactac gatacgggag ggcttaccat ctggcccccag    7920 tgctgcaatg ataccgcgag acccacgctc accggctcca gatttatcag caataaacca    7980
gccagccgga agggccgagc gcagaagtgg tcctgcaact ttatccgcct ccatccagtc    8040
tattaattgt tgccgggaag ctagagtaag tagttcgcca gttaatagtt tgcgcaacgt    8100
tgttgccatt gctacaggca tcgtggtgtc acgctcgtcg tttggtatgg cttcattcag    8160
ctccggttcc caacgatcaa ggcgagttac atgatccccc atgttgtgca aaaaagcggt    8220
tagctccttc ggtcctccga tcgttgtcag aagtaagttg gccgcagtgt tatcactcat    8280
ggttatggca gcactgcata attctcttac tgtcatgcca tccgtaagat gcttttctgt    8340
gactggtgag tactcaacca agtcattctg agaatagtgt atgcggcgac cgagttgctc    8400
ttgcccggcg tcaatacggg ataataccgc gccacatagc agaactttaa aagtgctcat    8460
cattggaaaa cgttcttcgg ggcgaaaact ctcaaggatc ttaccgctgt tgagatccag    8520
ttcgatgtaa cccactcgtg cacccaactg atcttcagca tctttacttt tcaccagcgt    8580
ttctgggtga gcaaaaacag gaaggcaaaa tgccgcaaaa aagggaataa gggcgacacg    8640
gaaatgttga atactcatac tcttcctttt tcaatattat tgaagcattt atcagggtta    8700
ttgtctcatg agcggataca tatttgaatg tatttagaaa aataaacaaa tagggggttcc    8760 gcgcacattt ccccgaaaag tgccacctga cg                                  8792
```

METHOD FOR PREPARING IMMUNOGLOBULIN LIBRARIES

CROSS-REFERENCE TO RELATED APPLICATIONS

This patent application is the national phase entry of PCT International Patent Application No. PCT/EP2006/066355, filed on Sep. 14, 2006, designating the United States of America, and published, in English, as PCT International Publication No. WO 2007/031550 A2 on Mar. 22, 2007, which PCT application claims priority from U.S. Provisional Patent application 60/717,685, filed Sep. 15, 2005, EP 05108488.7 filed Sep. 15, 2005, EP 05111782.8, filed Dec. 7, 2005, and EP 05111783.6 filed Dec. 7, 2005. Priority is also specifically claimed herein to U.S. Provisional Patent application 60/717,685, filed Sep. 15, 2005 under 35 U.S.C. §119 (e).

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "sequencelisting.txt" which is 74 KB and created on Feb. 14, 2008.

FIELD OF THE INVENTION

The invention relates to the preparation of immunoglobulin libraries from specific cell populations. In particular, the invention relates to the identification and generation of immunoglobulins derived from these immunoglobulin libraries having a specific functionality of interest.

BACKGROUND OF THE INVENTION

The alarming rise in serious antibiotic-resistant bacterial infections is generally acknowledged as a public health crisis. Of the estimated two million hospital infections in the United States in 2004, 70% were resistant to at least one antibiotic. Gram-positive bacteria belonging to three genera (*staphylococcus, streptococcus* and *enterococcus*) together cause more than 60% of all bloodstream infections (Wisplinghoff et al., 2004) and have acquired multi-drug resistance (e.g., methicillin-resistant *Staphylococcus aureus* (MRSA) and vancomycin-resistant *enterococci* (VRE)), thereby causing major medical and, consequently, economic problems. This trend is largely attributed to the indiscriminate use of antibiotics in the medical and veterinary field, which has greatly accelerated the accumulation and exchange of genetic information coding for antibiotic resistance in pathogenic bacteria (Dancer, 2004).

Despite the urgent need for the development of new antibiotics, the major pharmaceutical companies appear to have lost interest in the antibiotic market. In 2002, only five out of the more than 500 drugs in phase II or phase III clinical development were new antibiotics. In the last six years, only ten antibiotics have been registered and only two of those did not exhibit cross-reactivity with existing drugs (Spellberg et al., 2004). This trend has been attributed to several factors, e.g., the cost of new drug development and the relatively small return on investment that infectious disease treatments yield compared to drugs against hypertension, arthritis and lifestyle drugs, e.g., for impotence. Another contributing factor is the increasing difficulty in finding new targets, further driving up development costs. Therefore, investigation into novel therapies or preventative measures for multi-drug-resistant bacterial infections is urgently needed to meet this impending healthcare crisis.

Active immunization with vaccines and passive immunization with immunoglobulins are promising alternatives to classical small molecule therapy. A few bacterial diseases that once caused widespread illness, disability and death can now be prevented through the use of vaccines. The vaccines are based on weakened (attenuated) or dead bacteria, components of the bacterial surface or on inactivated toxins. The immune response raised by a vaccine is mainly directed to immunogenic structures, a limited number of proteins or sugar structures on the bacteria that are actively processed by the immune system. Since these immunogenic structures are very specific to the organism, the vaccine needs to comprise the immunogenic components of all variants of the bacteria against which the vaccine should be protective. As a consequence thereof, vaccines are very complex, take long and are expensive to develop. Further complicating the design of vaccines is the phenomenon of "antigen replacement." This occurs when new strains become prevalent that are serologically and, thus, antigenically distinct from those strains covered by the vaccines.

Direct administration of therapeutic immunoglobulins, also referred to as passive immunization, does not require an immune response from the patient and, therefore, gives immediate protection. In addition, passive immunization can be directed to bacterial structures that are not immunogenic and that are less specific to the organism. Passive immunization against pathogenic organisms has been based on immunoglobulins derived from sera of human or non-human donors. However, blood-derived products have potential health risks inherently associated with these products. In addition, the immunoglobulins can display batch-to-batch variation and may be of limited availability in case of sudden mass exposures. Recombinant-produced antibodies do not have these disadvantages and thus offer an opportunity to replace immunoglobulins derived from sera.

Over the last decade, a variety of recombinant techniques have been developed that have revolutionized the generation of antibodies and their engineering. Particularly, the development of antibody libraries and display technologies, such as phage display, or more recently developed display technologies, such as ribosome, yeast and bacterial display, have greatly influenced antibody preparation. In general, the established generation of antibody libraries in phages includes the cloning of repertoires of immunoglobulin genes or parts thereof for display on the surface of the phages. The starting material for preparing antibody libraries has been RNA isolated from the total population of peripheral blood lymphocytes or B cells from immunized or non-immunized donors. A problem associated with the use of the total population of peripheral blood lymphocytes or B cells for preparing antibody libraries is that functionally relevant and therapeutically effective antibodies against pathogenic organisms such as bacteria are underrepresented in these libraries.

This problem has now been solved by using RNA from a subset of antibody-producing B cells, i.e., IgM memory B cells, for the production of antibody libraries. Pathogenic organisms are known to have evolved many evasive techniques to avoid detection or attack from the immune system.

For example, many bacteria display huge variation in their surface antigens or at least the antigenic sites on which the immune system focuses. Therefore, antibodies designed to protect against these bacteria should be capable of recognizing many antigens to provide the maximum coverage of the most common infections; however, because of extensive antigen variation, coverage of all strains of a type of bacterium by an antibody is difficult to accomplish. Furthermore, although antibodies that are cross-reactive between strains are required, antibodies that are additionally cross-reactive between species of bacteria are preferred as these would be more attractive to develop and use clinically.

T lymphocyte help is known to be an important feature of adaptive immunity. Activated by vaccination or infection, adaptive immune responses are directed against a limited set of immunogenic epitopes in a process that takes weeks to fully develop. Once complete, a population of memory B cells that have switched their surface immunoglobulin receptor from M to another subtype, e.g., G (switched memory B cells or alternatively called IgG memory B cells), is generated and primed to respond with the secretion of a variety of high-affinity protective antibodies specifically against the infectious organism responsible for the initial infection or for which the vaccination was carried out.

In contrast, innate immunity refers to defense mechanisms that a host mounts immediately or within several hours after exposure to antigen expressed by a pathogen (Germain, 2004). Unlike adaptive immunity, innate immunity does not have the capacity to recognize every possible antigen presented to it. Instead, it has evolved to recognize a few highly conserved structures present in many different microorganisms. Memory B cells expressing the immunoglobulin M surface receptor (IgM memory B cells) behave more like an arm of innate immunity. They are stimulated independent of T cell help and develop and mutate their immunoglobulin genes during early childhood (<2 years of age).

The end result of this process is a diverse and protective pre-immune repertoire that is capable of responding immediately to a wide variety of pathogenic organisms and is particularly important in protection against encapsulated bacteria. Thus, libraries constructed from immunoglobulin genes derived from IgM memory B cells comprise an antibody repertoire applicable to potentially all pathogenic organisms, regardless of the infection and vaccination history of the donors, and would give rise to a new generation of antibodies suitable for combating the growing problem of pathogenic organisms such as bacteria.

IgM memory B cell-derived immunoglobulin libraries have the added advantage that it is not necessary to have access to donors with specific infections, which in some cases, such as with emerging infectious diseases, may be difficult to locate and recruit. Moreover, making antibody libraries from RNA obtained from IgM memory B cells reduces the library size needed to encompass the entire functionally relevant repertoire. IgM memory B cells comprise only around 25% of the total B cell population and further contain less immunoglobulin mRNA than circulating blast cells and, thus, may be further underrepresented in a total B cell library. Moreover, the antibody libraries derived from RNA obtained from IgM memory B cells only comprise mutated heavy and light chain variable region sequences and do not comprise germline-encoded antibody products, meaning that the libraries are focused on the most functionally relevant antibodies that have gone through a maturation process.

SUMMARY OF THE INVENTION

The invention provides methods for generating immunoglobulin libraries by isolating RNA from a subset of B cells. The immunoglobulin libraries are used to identify and obtain immunoglobulins having a specific functionality of interest.

Figure 1:
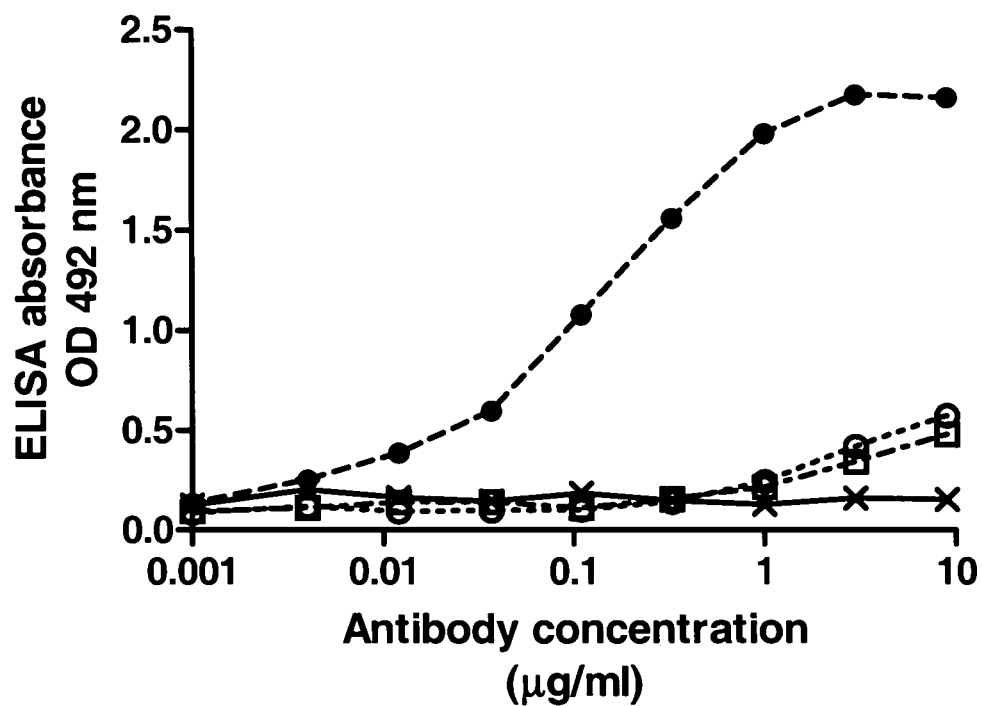
FIG. 1 shows binding of human immunoglobulins to H5 hemagglutinin, more specifically, titration of the anti-H5 IgGs CR5108 (○), CR5109 (□), CR5111 (●) dotted lines) and a control anti-WNV IgG (X) (solid line). The binding is indicated as the absorbance at 492 nm on the y-axis.

FIG. 2 shows the specificity of CR5111 to H5 hemagglutinin as measured by FACS analysis of transfected PER.C6® cells expressing hemagglutinin. PER.C6® cells transfected with hemagglutinin-expression vectors (H5TV, H5IC) or a vector expressing an irrelevant membrane protein (control) were stained with antibody CR5111 (right panels) or an isotype control antibody (left panels).

FIG. 3 shows Western blotting of hemagglutinin using CR5111. Proteins from hemagglutinin-expressing PER.C6® lysates were subjected to 10% reducing SDS-PAGE analysis, transferred to PVDF membrane followed by CR5111/horseradish peroxidase (HRP) labeled anti-human IgG or murine polyclonal anti-hemagglutinin IgG/HRP-labeled anti-mouse IgG.

FIG. 4 shows binding of human IgGs to C-Ps, more specifically, titration of the anti-C-Ps IgGs CR50095 (●), CR5097 (□), CR5098 (Δ), CR5114 (○) dotted lines) and a control anti-WNV IgG (X) (solid line). The binding is indicated as the absorbance at 492 nm on the y-axis.

DETAILED DESCRIPTION OF THE INVENTION

In a first aspect, the present invention encompasses a method for generating an immunoglobulin library by isolating RNA from B cells and preparing the immunoglobulin library from the RNA, characterized in that the RNA is isolated from a subset of B cells. The term “subset of B cells” means that, instead of the whole/complete population of B cells, one or more specific subgroups/compartments of B cells are specifically used for RNA isolation. In other words, the RNA used for preparing the immunoglobulin libraries is derived from a specific group of B cells and not from the total population of B cells. These subsets are selected and/or isolated. As a consequence thereof, other subsets of B cells are excluded. If necessary, several different subsets can be mixed before isolating the RNA.

The subset of B cells can be derived from B cells obtained from peripheral blood or a fraction thereof, such as peripheral blood lymphocytes. Alternatively, the subset can be obtained from spleen, bone marrow, tonsils, lymphoid tissues, tissues including peyers patches, gut-associated and mucosal-associated lymphoid tissues and mucosal tissue. The subset of B cells is memory B cells. Naïve B cells carrying IgM surface receptors are not selected and thus excluded. The group of memory B cells can be further subdivided into IgM memory B cells and switch memory B cells (mainly IgG memory B cells).

In the invention, the subset of B cells are IgM memory B cells. In other words, the invention provides a method for generating an immunoglobulin library by isolating RNA from a subset of B cells and preparing the immunoglobulin library from the RNA, characterized in that the subset of B cells consists essentially of IgM memory B cells. “Essentially consisting of," as used herein, means that at least 90%, preferably at least 92%, more preferably at least 95% and, in particular, 97% of the B cells in the subset are IgM memory B cells. The specific subsets of B cells can be distinguished and/or isolated from other B cells by making use of their specific cell surface phenotype, by size or by density. For example, all memory B cells can be identified and/or isolated by the expression of cell surface molecules including, but not limited to, CD19, CD20, CD21, CD22, CD24, CD27, CD39, CD80, CD86, CD95, CD148 and combinations thereof. The IgM memory B cells can be distinguished and/or isolated from switch memory B cells by the expression of molecules including, but not limited to, IgM, IgD, CD1c and combinations thereof. Plasma blast cells can be identified and/or isolated from other B cells by the high expression of CD38 and/or the expression of molecules including, but not limited to, CD19, CD21, CD39, CD138, VLA-4 and combinations thereof, and the absence of expression of molecules including, but not limited to, CD10, CD20, CD24, CD5, VLA-5, MPC-1 and combinations thereof.

In general, B cells develop in the bone marrow from a common lymphopoetic precursor and migrate as transitional B cells via the bloodstream to the spleen or lymph node. In the spleen, they further develop to long-lived mature B cells, which recirculate in the lymphoid follicles of spleen, blood and lymph node. After encountering pathogenic antigens, certain B cells are recruited to the germinal centers and, in cooperation with Th cells, they start differentiating into high-affinity antibody-producing plasma B cells. These activated B cells first produce multimeric low-affinity IgM antibodies and later, after Th cell-induced class switch, high-affinity monomeric IgG (or IgA or IgE) molecules. The antibody-producing plasma cells, home to the bone marrow and a small proportion of the activated B cells, turn into long-lived memory cells that circulate through blood, spleen and lymph node follicles (switched memory B cells). This response is very specific, but slow. Apart from the above-described T cell-dependent B cell response, another B cell subset residing in the marginal zone of the spleen proliferates in a Th-independent manner to pathogenic stimulation and form foci of plasma blasts producing IgM antibodies (IgM memory B cells). This IgM response represents a direct first-line defense against blood-born infections and the only one against encapsulated bacteria.

The term "immunoglobulin," as used herein, includes all immunoglobulin classes and subclasses known in the art including IgA, IgD, IgE, IgG, and IgM, and their subclasses (isotypes), e.g., IgA1, IgA2, IgG1, IgG2, IgG3 and IgG4. Preferably, the immunoglobulins of the invention are human immunoglobulins. Also, an antigen-binding and/or variable domain comprising fragment of an immunoglobulin is meant. Antigen-binding fragments include, inter alia, Fab, F(ab'), F(ab')2, Fv, dAb, Fd, complementarity-determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc.

The above fragments may be produced synthetically or by enzymatic or chemical cleavage of intact immunoglobulins or they may be genetically engineered by recombinant DNA techniques. The methods of production are well known in the art and are described, for example, in *Antibodies: A Laboratory Manual*, edited by E. Harlow and D. Lane (1988), Cold Spring Harbor Laboratory, Cold Spring Harbor, N.Y., which is incorporated herein by reference. An immunoglobulin or antigen-binding fragment thereof may have one or more binding sites. If there is more than one binding site, the binding sites may be identical to one another or they may be different.

In an embodiment of the invention, the subset of B cells, e.g., IgM memory B cells, is derived from several individuals. Preferably, however, the subset of B cells is derived from a single individual. The subset can be derived from a single individual at various different time points. The individual can be an animal including, but not limited to, mouse, rat, chicken, cow, monkey, horse, goat, sheep, pig, dog, rabbit, etc. Preferably, the individual is a human. The individual can be healthy, convalescent, known to have recovered, or still suffering from a disease state.

In an embodiment of the invention, the disease can be associated with a pathogenic organism. The individual might be infected with, e.g., a pathogenic organism but does still not manifest full disease symptoms. The individual can be immunized or non-immunized. The individual can be vaccinated against or exposed to a pathogenic organism or part thereof. In an embodiment, the pathogenic organism is selected from the group consisting of a virus, a bacterium, a yeast, a fungus, a protozoa and a parasite. In general, blood is first recruited from donors. For vaccinated donors, blood will be preferably drawn six to seven, more preferably ten, days after the last boost. The composition of the B cell repertoire may be used to select the most favorable donor(s) from the panel. Selection criteria are a high or even the highest percentage of the specific subset of B cells of interest, IgM memory B cells. The percentage of the specific subset of B cells should be at least 0.5%, preferably at least 1%, more preferably at least 2% and, in particular, at least 5% of the total population of lymphocytes of a given donor. Next, the specific subset of B cells is isolated from the blood or fraction thereof of one or more individuals by means of methods suitable for isolating specific subsets of B cells such as FACS sorting or panning using antibodies against cell type markers coated to beads, e.g., magnetic beads or streptavidin-coated beads. If necessary, the isolated subset of cells may be cultured before use.

In another embodiment of the invention, the immunoglobulins of the immunoglobulin libraries of the invention are displayed on the surface of replicable genetic packages. A "replicable genetic package," as used herein, can be prokaryotic or eukaryotic and includes cells, spores, bacteria, viruses, yeasts, fungi, (bacterio)phages, ribosomes, and polysomes. A preferred replicable genetic package is a (bacterio)phage. The immunoglobulins, such as, for instance, single-chain Fvs, are displayed on the replicable genetic package, i.e., they are attached to a group or molecule located at an exterior surface of the replicable genetic package. The replicable genetic package is a screenable unit comprising an immunoglobulin to be screened linked to a nucleic acid molecule encoding the immunoglobulin. The nucleic acid molecule should be replicable either in vivo (e.g., as a vector) or in vitro (e.g., by PCR, transcription and translation). In vivo replication can be autonomous (as for a cell), with the assistance of host factors (as for a virus) or with the assistance of both host and helper virus (as for a phagemid). Replicable genetic packages displaying a collection of immunoglobulins are formed by introducing nucleic acid molecules encoding exogenous immunoglobulins to be displayed into the genomes of the replicable genetic packages to form fusion proteins with endogenous proteins that are normally expressed from the outer surface of the replicable genetic packages. Expression of the fusion proteins, transport to the outer surface and assembly results in display of exogenous binding molecules from the outer surface of the replicable genetic packages.

In a specific embodiment of the invention, the immunoglobulin library is selected from the group consisting of an antibody library, a single chain Fv library and a Fab library.

A further aspect of the invention is directed to a method of generating an immunoglobulin library according to the invention, wherein the method comprises the steps of: isolating a subset of B cells, e.g., IgM memory B cells, from an individual, isolating RNA from the subset of B cells, converting the isolated RNA into cDNA, amplifying immunoglobulin sequences of the cDNA, inserting the amplified immunoglobulin sequences into at least one vector, and transforming at least one host cell with the at least one vector containing the amplified sequences to obtain an immunoglobulin library. Optionally, before isolating the subset of B cells peripheral blood lymphocytes can be isolated from the blood derived from an (single) individual.

In a preferred embodiment, the subset of B cells is isolated by means of FACS sorting by staining the peripheral mononuclear cells with antibodies against memory B cell markers such as CD24 and CD27 and IgM or IgD. Cells expressing this phenotype are defined as IgM memory cells. Cell expressing CD24 and CD27, but not IgM or IgD, are defined as switched memory cells (mainly IgG memory cells). Both cell populations can be sorted together or separately into tubes for RNA extraction.

In an embodiment of the invention, the subset of B cells that is used for RNA isolation comprises at least 10,000 cells, preferably at least 25,000 cells, more preferably at least 50,000 cells, even more preferably at least 75,000 cells and particularly at least 100,000 cells. The subset of B cells used for RNA isolation can be up to $1\times10^7$ cells. Optionally, at least two of the three steps of: isolating RNA from the subset of B cells, converting the isolated RNA into cDNA, and amplifying immunoglobulin sequences of the cDNA can be performed in a single step. A repertoire of immunoglobulin genes of an individual may be sythesized from the subset of B cells using polymerase chain reaction (PCR) technology; however, other amplification methods may, of course, also be used. In the practice of the invention, immunoglobulin libraries are typically prepared by first synthesizing cDNAs from total RNA using random hexamer primers.

Alternatively, mRNA could first be separated from the other RNAs isolated and used for conversion into cDNA. Immunoglobulin genes are then amplified by PCR using specific primers for the different $V_H$ and $V_L$ gene families and IgG constant domains, IgM constant domains or other primers. The immunoglobulin cDNAs so produced are then ligated into at least one vector. Alternatively, the genes encoding the immunoglobulins are amplified directly from the subset of B cells (without any nucleic acid recovery step before amplification). Suitable vectors are known to a person skilled in the art. Preferred vectors include phage vectors or phagemids. It is clear that the vectors comprise polynucleotide sequences necessary for and/or affecting the expression of an operably linked coding sequence in a particular host organism. At least one host cell is transformed with the at least one vector containing the cDNAs to obtain a library. Then, the library obtained can be screened for immunoglobulins of interest. Alternatively, immunoglobulin libraries obtained from different individuals can be pooled and subjected to screening for immunoglobulins of interest.

The cDNA encoding the immunoglobulins of interest can be inserted into at least one expression vector that can be transfected into at least one host cell. Finally, the tranfected host cells can be cultured under conditions conducive to the expression of the immunoglobulins of interest and, optionally, the expressed immunoglobulins are recovered. The expressed immunoglobulins can be recovered from the cell free extract, but preferably, they are recovered from the culture medium. Methods to recover proteins, such as immunoglobulins, from cell free extracts or culture medium are well known to the man skilled in the art. Suitable expression vectors, as well as suitable host cells, are also known to a skilled artisan. Preferred host cells are mammalian cells including human retina cells such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B.V.). For the purposes of this application "PER.C6" refers to cells deposited under number 96022940 or ancestors, passages up-stream or down-stream, as well as descendants from ancestors of deposited cells, as well as derivatives of any of the foregoing. It is clear for the person skilled in the art that alternative methods exist for producing immunoglobulins.

Phage display methods for identifying and obtaining immunoglobulins, e.g., (monoclonal) antibodies, are by now well-established methods known by the person skilled in the art. They are, e.g., described in U.S. Pat. No. 5,696,108; Burton and Barbas, 1994; de Kruif et al., 1995; and *Phage Display: A Laboratory Manual*, edited by C. F. Barbas, D. R. Burton, J. K. Scott and G. J. Silverman (2001), Cold Spring Harbor Laboratory Press, Cold Spring Harbor, N.Y. All these references are herewith incorporated herein in their entirety. For the construction of phage display libraries, collections of immunoglobulin heavy- and light-chain variable region genes are expressed on the surface of bacteriophage, preferably filamentous bacteriophage particles in, for example, single-chain Fv (scFv) or in Fab format (see de Kruif et al., 1995). Libraries of antibody fragment-expressing phages may be assembled from the immunoglobulin V regions expressed in the B lymphocytes of individuals. In a specific embodiment of the invention, the phage library of immunoglobulins, preferably scFv phage library, is prepared from RNA isolated from a specific subset of B cells, e.g., IgM memory B cells, obtained from a single individual.

Specific phage antibodies can be selected from the libraries by immobilizing target antigens, such as antigens from pathogenic organisms, on a solid phase and subsequently exposing the target antigens to a phage library to allow binding of phages expressing antibody fragments specific for the solid phase-bound antigen(s). Non-bound phages are removed by washing and bound phages eluted from the solid phase for infection of *Escherichia coli (E. coli)* bacteria and subsequent propagation. Multiple rounds of selection and propagation are usually required to sufficiently enrich for phages binding specifically to the target antigen(s). In the multiple selection rounds, identical or different antigens can be used.

If desired, before exposing the phage library to target antigens, the phage library can first be subtracted by exposing the phage library to non-target antigens bound to a solid phase. These non-target antigens may be closely related to the target antigens. Antigens used for selecting phages may also be complex antigens, such as complex mixtures of proteins, (poly)peptides or other structures of pathogenic organisms, host cells expressing one or more proteins, (poly)peptides or other structures of pathogenic organisms, or complete (active, inactivated, attenuated or otherwise manipulated) pathogenic organisms. The pathogenic organisms or antigens thereof can be isolated or non-isolated and may be manipulated before use.

Purification may be performed by means of well-known purification methods suitable for pathogenic organisms or their antigens. These are well known to a person skilled in the art. A person skilled in the art is, of course, aware that the libraries of the invention can also be selected on antigens other than antigens from pathogenic organisms, such as tumor antigens and (poly)peptides of different nature to name just a few. Even cells such as tumor cells can be used for selection purposes.

Antigen-specific phage antibodies can be selected from the library by incubating an antigenic structure of a pathogenic organism with the phage antibody library to let, for example, the scFv or Fab part of the phage bind to the antigenic structure. After incubation and several washes to remove unbound and loosely attached phages, the phages that have bound with their scFv or Fab part to the preparation are eluted and used to infect *Escherichia coli* to allow amplification of the new specificity. Generally, one or more selection rounds, either with the same antigenic structures or with different antigenic structures, are required to separate the phages of interest from the large excess of non-binding phages. Proteins or (poly) peptides of the pathogenic organism can be expressed in host cells and these cells can be used for selection of phage antibodies specific for the pathogenic organism. A phage display method can be extended and improved by subtracting non-relevant binders before, during or after screening by addition of (an excess of) host cells comprising no target molecules or non-target molecules that are similar, but not identical, to the target, and thereby strongly enhance the chance of finding relevant binding molecules. (This process is referred to as the MAbstract® process. MAbstract® is a registered trademark of Crucell Holland B.V. See also, U.S. Pat. No. 6,265,150, which is incorporated herein by reference.)

Once a new scFv or Fab has been established or identified, the DNA encoding the scFv or Fab can be isolated from the bacteria or phages and combined with standard molecular biological techniques to make constructs encoding complete human immunoglobulins of a desired specificity (e.g., IgG, IgA or IgM). These constructs can be transfected into suitable cell lines and complete human monoclonal antibodies can be produced (see Huls et al., 1999; Boel et al., 2000).

In another aspect, the invention pertains to a method of identifying an immunoglobulin having a functionality of interest from an immunoglobulin library according to the invention. The method comprises the steps of generating an immunoglobulin library prepared from RNA isolated from a subset of B cells, being IgM memory B cells, screening the immunoglobulin library obtained for an immunoglobulin having the functionality of interest and optionally isolating an immunoglobulin having the functionality of interest. The functionality of interest can be selected from the group consisting of antigen specificity, binding affinity, neutralizing activity, opsonic activity, fusion inhibition, complement fixing activity, recruitment and attachment of immune effector cells and intrinsic bactericidal activity. In an embodiment, the functionality of interest is specificity for H5N1, more specifically specificity for HA of H5N1 and, even more specifically, specificity for HA1 of H5N1.

In an embodiment of the invention, the method comprises the steps of contacting an immunoglobulin library prepared from RNA isolated from a subset of B cells with one or more antigens under conditions conducive to binding, separating and recovering immunoglobulins that bind to the one or more antigens from immunoglobulins that do not bind, isolating at least one recovered immunoglobulin, screening if the immunoglobulin isolated has a functionality of interest, and isolating the immunoglobulin having the functionality of interest. An immunoglobulin obtainable by a method as described above is another aspect of the invention.

In another aspect, the invention is concerned with an immunoglobulin library obtainable by a method according to the invention. The library of the invention can be a combinatorial library. Furthermore, the invention is directed to an immunoglobulin library comprising 6% or less (i.e., not more than 6%) germline immunoglobulin sequences. In other words, the library of the invention comprises from 0-6%, preferably from 0-5%, from 0-4%, from 0-3%, from 0-2%, or from 0-1% immunoglobulin sequences having germline sequences. In an embodiment, the immunoglobulin library of the invention comprises no germline immunoglobulin sequences.

The immunoglobulin libraries of the invention are rearranged antibody gene libraries from differentiated B cells, e.g., IgM memory B cells. That is, variable region sequences from the libraries have non-silent mutations, most commonly in the complementarity-determining regions but also in the framework regions, that distinguish them from the rearranged germline precursor sequences present in newly differentiated B cells and represented in chromosomal DNA of the respective donor.

The immunoglobulin library according to the invention comprises at least one mutation in the (rearranged) germline precursor immunoglobulin sequences. Preferably, the immunoglobulin library according to the invention comprises immunoglobulin sequences comprising at least one mutation in the variable region (excluding the CDR3 region), preferably the heavy chain variable region, when compared to the variable region of the (rearranged) germline precursor immunoglobulin sequences. In an embodiment, the library of the invention comprises from 94-100%, preferably from 95-100%, 96-100%, 97-100%, 98-100%, or 99-100% immunoglobulin sequences having a mutation in their amino acid sequence when compared to the germline amino acid sequence. Preferably, the amino acid mutation is in the variable region (excluding the CDR3 region), preferably the heavy chain variable region.

In an embodiment, the library of the invention comprises only immunoglobulins having mutations in their amino acid sequences (when compared to the germline sequences), preferably in the amino acid sequences of the heavy chain variable regions. Individual germline antibodies may display configurational diversity that allows diverse binding patterns and even polyspecificity. In a preferred embodiment, the immunoglobulin libraries of the invention are essentially derived from IgM sequences. In the case of IgM memory B cells, it is not clear what is driving the mutation of their immunoglobulin sequences, but it may also generate antibodies of higher potency and specificity. In addition, mutated immunoglobulin sequences are preferred for combinational libraries because the mutation of heavy- and light-chain variable regions is a cooperative process and, thus, individual variable regions will preferentially bind with their mutated partner, resulting in libraries with a greater frequency of favorably paired heavy and light chains.

In contrast, germline genes, as discussed above, show greater conformational plasticity and, therefore, introduce less favorable pairing of heavy and light chains. Preferably, the library is natural and not a synthetic or semi-synthetic antibody library. If IgM memory B cells are used as starting material for isolating RNA, the immunoglobulin libraries contain IgM-derived immunoglobulin sequences.

In yet another aspect, the invention is directed to the use of RNA isolated from a subset of B cells, IgM memory B cells, for the preparation of an immunoglobulin library. Moreover, the invention is directed to the use of a subset of B cells, IgM memory B cells, for the preparation of an immunoglobulin library. In an embodiment, the B cells are IgM memory B cells.

The invention is also directed to the use of an immunoglobulin library according to the invention for the identification and/or isolation of an immunoglobulin having a functionality of interest and to the immunoglobulins so identified and/or isolated.

EXAMPLES

To illustrate the invention, the following examples are provided. The examples are not intended to limit the scope of the invention in any way.

Example 1

Construction of scFv Phage Display Libraries Using RNA Extracted from Memory B Cells Peripheral blood was collected from normal healthy donors, convalescent donors or vaccinated donors by venapunction using EDTA anti-coagulation sample tubes. A blood sample (45 ml) was diluted twice with PBS and 30 ml aliquots were underlayed with 10 ml Ficoll-Hypaque or Ficoll-Paque Plus (GE-Healthcare) and centrifuged at 900×g for 20 minutes at room temperature without breaks. The supernatant was removed carefully to just above the white layer containing the lymphocytic and thrombocytic fraction. Next, this layer was carefully removed (~10 ml), transferred to a fresh 50 ml tube and washed three times with 40 ml PBS and spun at 400×g for ten minutes at room temperature to remove thrombocytes. The obtained pellet-containing lymphocytes was resuspended in RPMI medium containing 2% FBS and the cell number was determined by cell counting. Approximately 1×10$^8$ lymphocytes were stained for fluorescent cell sorting using CD24, CD27 and surface IgM as markers for the isolation of switched and IgM memory B cells. A Becton Dickinson Digital Vantage apparatus set in Yield Mode was used for physical memory B cell sorting and isolation. Lymphocytes were gated as the small compact population from the FSC/SSC window. Memory B cells (CD24+/CD27+) were subsequently separated from naive B cells (CD24+/CD27−) and memory T cells (CD24−/CD27+).

In a next step, IgM memory B cells (IgM+) were separated from switch memory B cells (IgM−) using IgM expression. In this step, IgM memory B cells and switch memory B cells were sorted in separate sample tubes. 1×10$^5$ cells of each population were collected in DMEM/50% FBS and after completion of the sort, they were each centrifuged at 400×g for ten minutes and lysed in 500 µl TRIZOL total RNA extraction solution (Invitrogen). The RNA was extracted from the lysis solution using 200 µl chloroform and isopropanol precipitation as detailed in the TRIZOL solution protocol. Next, 1 µl Pellet Paint (Novagen) was applied to enhance and visualize the pelleting process. The complete RNA preparation was dissolved in 23 µl DEPC-treated ultrapure water (Invitrogen) and used for cDNA conversion with SuperScript III Reverse Transcriptase (Invitrogen). One µl Random Hexamers (500 ng/µl) (Promega) was added to the RNA sample and mixed and melted at 65° C. for five minutes in a heated lid PCR machine. The sample was snap-cooled on wet-ice and the following components were added: 8 µl 5×RT buffer (250 mM Tris/HCl pH 8.3, 375 mM KCl, 15 mM MgCl$_2$), 2 µl dNTPs (10 mM of each) (Invitrogen), 2 µl DTT (100 mM), 2 µl RNAse Inhibitor (40 U/µl) (Promega), 2 µl SuperScript III (200 U/µl) (Invitrogen). The obtained mixture was first incubated for five minutes at room temperature and then transferred to a heated lid PCR machine at 50° C. for one hour. The reaction was stopped by heating up to 75° C. for 15 minutes. The cDNA obtained was diluted to 200 µl with ultrapure water and stored at −20° C. until further use.

A two round PCR amplification approach was applied using the primer sets shown in Tables 1 and 2 to isolate the immunoglobulin VH and VL regions from the respective donor repertoire. The PCR formulation for amplification used throughout the procedure was as follows: 5 µl cDNA template, 32.75 µl ultrapure water, 2.5 µl of each primer (10 µM), 5 µl 10×PCR buffer (200 mM Tris/HCl pH 8.4, 500 mM KCl), 2.5 µl MgCl$_2$ (50 mM), 0.5 µl dNTPs (25 mM of each), 0.25 µl Taq polymerase (5 U/µl) (Invitrogen). First round amplification on the respective cDNA using the primer sets mentioned in Table 1 yielded seven, six and nine products of about 650 base pairs for respectively $V_H$, Vκ and Vλ regions. For IgM memory B cell cDNA amplification, the OCM constant primer was used in combination with OH1 to OH7, while for switch memory B cells, the OCG primer was combined with OH1 to OH7. The thermal cycling program for first round amplifications was: two minutes at 96° C. (denaturation step); 30 cycles of 30 seconds at 96° C., 30 seconds at 55° C., and 60 seconds at 72° C.; ten minutes at 72° C. final elongation; and 4° C. refrigeration. The products were loaded on and isolated from a 1%-agarose gel using gel-extraction columns (Qiagen) and eluted in 50 µl 1 mM Tris/HCl pH 8.0. Ten percent of first round products (5 µl) was subjected to second round amplification using the primers mentioned in Table 2. These primers were extended with restriction sites enabling the directional cloning of the respective $V_L$ and $V_H$ regions into phage display vector PDV-C06.

The PCR program for second round amplifications was as follows: two minutes at 96° C. (denaturation step); 30 cycles of 30 seconds at 96° C., 30 seconds at 60° C., 60 seconds at 72° C.; ten minutes at 72° C. final elongation; and 4° C. refrigeration. The second round V-J products (~350 base pairs) were first pooled according to natural occurrence of J segments found in immunoglobulin gene products, resulting in seven, six and nine pools for, respectively, the $V_H$, Vκ and Vλ variable regions (see Tables 3 and 4).

To obtain a natural distribution of immunoglobulin sequences in the immune library, the six Vκ and nine Vλ light-chain pools were mixed according to the percentages mentioned in Table 3. This single final $V_L$ pool (3 µg) was digested overnight with SalI and NotI restriction enzymes, loaded on and isolated from a 1.5%-agarose gel (~350 base pairs) using Qiagen gel-extraction columns and ligated in similarly cut PDV-C06 vector (~5000 base pairs) as follows: 10 µl PDV-C06 vector (50 ng/µl), 7 µl $V_L$ insert (10 ng/µl), 5 µl 10× ligation buffer (NEB), 2.5 T4 DNA Ligase (400 U/µl) (NEB), 25.5 µl ultrapure water (vector to insert ratio was 1:2). Ligation was performed overnight in a water bath of 16° C.

Next, the volume was doubled with water, extracted with an equal volume of phenol-chloroform-isoamylalcohol (75: 24:1) (Invitrogen) followed by chloroform (Merck) extraction and precipitated with 1 µl Pellet Paint (Novagen), 10 ul sodium acetate (3 M pH 5.0) and 100 µl isopropanol for two hours at −20° C. The obtained sample was subsequently centrifuged at 20,000×g for 30 minutes at 4° C. The obtained precipitate was washed with 70% ethanol and centrifuged for ten minutes at 20,000×g at room temperature. Ethanol was removed by vacuum aspiration and the pellet was air dried for several minutes and then dissolved in 50 µl buffer containing 10 mM Tris/HCl, pH 8.0. One µl ligation mixture was used for the transformation of 40 µl TG-1 electro-competent cells (Stratagene) in a chilled 0.1 cm electroporation cuvette (Biorad) using a Genepulser II apparatus (Biorad) set at 1.7 kV, 200 Ohm, 25 µF (time constant ~4.5 msec).

Directly after pulse, the bacteria were flushed from the cuvette with 1000 µl SOC medium (Invitrogen) containing 5% (v/v) glucose (Sigma) at 37° C. and transferred to a 15 ml round bottom culture tube. Another 500 µl SOC/glucose was used to flush residual bacteria from the cuvette and was added to the culture tube. Bacteria were recovered by culturing for exactly one hour at 37° C. in a shaker incubator at 220 rpm. The transformed bacteria were plated over large 240 mm square petridishes (NUNC) containing 200 ml 2TY agar (16 g/l bacto-tryptone, 10 g/l bacto-yeast extract, 5 g/l NaCl, 15 g/l agar, pH 7.0) supplemented with 100 µg/ml Ampicillin and 5% (v/v) Glucose (Sigma). A 1 to 1000 dilution was plated for counting purposes on 15 cm petridishes containing the same medium.

This transformation procedure was repeated sequentially twenty times and the complete library was plated over a total of thirty large square petridishes and grown overnight in a 37° C. culture stove. Typically, around $1 \times 10^7$ cfu were obtained using the above protocol. The intermediate $V_L$ light-chain library was harvested from the plates by mildly scraping the bacteria into 10 ml 2TY medium per plate. The cell mass was determined by OD 600 measurement and two times 500 OD of bacteria was used for maxi plasmid preparation using two P500 maxiprep columns (Qiagen) according to the manufacturer's instructions.

Analogous to the $V_L$ variable regions, the second round $V_H$-$J_H$ products were first mixed together to obtain the normal J segment usage distribution (see Table 4), resulting in seven $V_H$ subpools called PH1 to PH7. The pools were mixed to acquire a natural sequence distribution using the percentages depicted in Table 4, obtaining one $V_H$ fraction that was digested with SfiI and XhoI restriction enzymes and ligated in the similarly cut PDV-VL intermediate library obtained as described above. The restriction digestion, ligation set-up, purification method, subsequent transformation of TG1 and harvest of bacteria was exactly as described for the $V_L$ intermediate library (see above).

The final library (approximately $1 \times 10^7$ cfu) was checked for insert frequency with a colony PCR using a primer set flanking the $V_H$-$V_L$ regions. More than 90% of the colonies showed a correct length insert (see Table 5). The colony PCR products were used for subsequent DNA sequence analysis to check sequence variation and to assess the percentage of colonies showing a complete ORF. This was typically above 70% (see Table 5). The frequency of mutations in the V genes was also analyzed. Out of 50 heavy chain sequences, only three (6%) were in germline configuration (i.e., 94% of the sequences contained mutations) indicative of a maturation process and consistent with the memory phenotype of the B cells used as an RNA source for the library. Finally, the library was rescued and amplified by using CT helper phages (see WO 02/103012) and was used for phage antibody selection by panning methods.

In addition, an IgM antibody phage display library was generated from RNA extracted from total peripheral blood lymphocytes (which include memory B cells) essentially as described above. Lymphocytes were isolated from blood by ficoll-paque separation. RNA was extracted and a variable heavy chain library was generated as described above. A single variable kappa light chain gene (L6) was used to partner with the heavy chain library. The library was rescued and amplified by using CT helper phages and was used for phage antibody selection by panning methods. The frequency of mutations in the V genes of the IgM antibody phage display library from RNA extracted from total peripheral blood lymphocytes was also analyzed. Around 30% of the heavy chain sequences were in germline configuration, i.e., around 70% contained mutations. From this was deduced that libraries made from IgM memory B cells comprise significantly more sequences containing mutations than libraries made from total peripheral blood lymphocytes.

Example 2

Selection of Phages Carrying Single Chain Fv Fragments Against Antigens

Antibody fragments were selected using antibody phage display libraries constructed essentially as described above and general phage display technology and MAbstract® technology essentially as described in U.S. Pat. No. 6,265,150 and in WO 98/15833 (both of which are incorporated by reference herein). Furthermore, the methods and helper phages as described in WO 02/103012 (which is incorporated by reference herein) were used in the present invention.

Selection was performed against recombinant hemagglutinin subtype H5 (A/Vietnam/1203/2004; Protein Sciences, CT, USA). This external antigen is expressed on the surface of avian influenza strains, but not human strains. The donors from whom the libraries were built had not been exposed to this antigen. H5 antigen was diluted in PBS (1.0 µg/ml).

In another experiment, selection was performed against an antigen from the cell wall of *Streptococcus pneumoniae*, Pneumococcal cell wall polysaccharide (C-Ps) (Statens serum institute, Denmark). It is known in the art that almost all individuals have antibodies against this antigen (see Musher et al., 1990). C-Ps was diluted in PBS (2.5 µg/ml).

Two to 3 ml of the antigen preparation was added to MaxiSorp™ Nunc-Immuno Tubes (Nunc) and incubated overnight at 4° C. on a rotating wheel. An aliquot of a phage display library (500 µl, $10^{13}$ cfu/ml, amplified using CT helper phage (see WO 02/103012)) was blocked in blocking buffer (2% Protifar in PBS) for one to two hours at room temperature. The blocked phage library was added to the immunotubes, incubated for two hours at room temperature, and washed with wash buffer (0.1% v/v Tween-20 in PBS) to remove unbound phages. Bound phages were eluted from the antigen by incubation with 1 ml of 50 mM glycine-HCl pH 2.2 for ten minutes at room temperature. Subsequently, the eluted phages were mixed with 0.5 ml of 1 M Tris-HCl pH 7.5 to neutralize the pH. This mixture was used to infect 5 ml of an XL1-Blue *E. coli* culture that had been grown at 37° C. to an OD 600 nm of approximately 0.3. The phages were allowed to infect the XL1-Blue bacteria for 30 minutes at 37° C. Then, the mixture was centrifuged for ten minutes at 3200*g at room temperature and the bacterial pellet was resuspended in 0.5 ml 2-trypton yeast extract (2TY) medium. The obtained bacterial suspension was divided over two 2TY agar plates supplemented with tetracyclin, ampicillin and glucose. After incubation overnight of the plates at 37° C., the colonies were scraped from the plates and used to prepare an enriched phage library, essentially as described by De Kruif et al. (1995a) and WO 02/103012. Briefly, scraped bacteria were used to inoculate 2TY medium-containing ampicillin, tetracycline and glucose and grown at a temperature of 37° C. to an OD 600 nm of ~0.3. CT helper phages were added and allowed to infect the bacteria, after which the medium was changed to 2TY-containing ampicillin, tetracycline and kanamycin. Incubation was continued overnight at 30° C. The next day, the bacteria were removed from the 2TY medium by centrifugation, after which the phages in the medium were precipitated using polyethylene glycol (PEG) 6000/NaCl.

Finally, the phages were dissolved in 2 ml of PBS with 1% bovine serum albumin (BSA), filter-sterilized and used for the next round of selection.

Two rounds of selections were performed before isolation of individual single-chain phage antibodies against the respective antigens. After the second round of selection, individual *E. coli* colonies were used to prepare monoclonal phage antibodies. Essentially, individual colonies were grown to log-phase in a 96-well plate format and infected with CT helper phages, after which phage antibody production was allowed to proceed overnight. The produced phage antibodies were PEG/NaCl-precipitated and filter-sterilized and tested in ELISA for binding to H5 antigen or C-Ps antigen.

Example 3

Validation of H5-Specific and C-Ps-Specific Single-Chain Phage Antibodies

Selected single-chain phage antibodies that were obtained in the screenings described above were validated in ELISA for specificity, i.e., binding to H5 antigen or binding to C-Ps antigen. Additionally, the single-chain phage antibodies were also tested for binding to a control antigen, Protifar milk powder. For this purpose, the antigens were coated to Maxisorp™ ELISA plates. After coating, the plates were blocked in PBS containing 2% BSA for one hour at room temperature. The selected single-chain phage antibodies were incubated for 15 minutes in an equal volume of PBS containing 2% BSA to obtain blocked phage antibodies. The plates were emptied and the blocked single-chain phage antibodies were added to the wells. Incubation was allowed to proceed for one hour, the plates were washed in PBS containing 0.1% v/v Tween-20 and bound phage antibodies were detected (using OD 492 nm measurement) using an anti-M13 antibody conjugated to peroxidase. As a control, the procedure was performed simultaneously without single-chain phage antibody and with a negative control single-chain phage antibody.

From the selections on the H5 antigen with the IgM memory B cell library, three single-chain phage antibodies specific for H5 and three single-chain phage antibodies reactive with H5 and Protifar milk powder were obtained (see Table 6). In contrast, no specific H5 binders were found in the selections with the IgM library constructed from RNA from total peripheral blood lymphocytes, but 17 phage antibodies cross-reactive with H5 and Protifar milk powder were selected (data not shown). The sequences of the antibodies selected from the IgM memory B cell library contained mutations in their VH gene with a high replacement to silent mutation ratio (see Table 7). This is an indication of an affinity maturation process and is a defining characteristic of antibodies derived from memory B cells. These results suggest that IgM memory B cell libraries contain diversified antibody repertoires. Furthermore, it was concluded that antibodies for an antigen to which the donors had no prior exposure can be selected from an IgM memory B cell library, while such antibodies were not obtained from an IgM library prepared from RNA from total peripheral blood lymphocytes.

From the selections on the C-Ps antigen, six single-chain phage antibodies specific for C-Ps and two single-chain phage antibodies reactive with C-Ps and Protifar milk powder were obtained (see Table 8). In contrast, in the selections with the IgM library constructed from RNA from total peripheral blood lymphocytes, only two single-chain phage antibodies specific for C-Ps and no cross-reactive phage antibodies were selected (see Table 9).

Example 4

Characterization of H5-Specific and C-Ps-Specific scFvs

From the selected specific single-chain phage antibody (scFv) clones specific for H5, plasmid DNA was obtained and nucleotide and amino acid sequences were determined according to standard techniques. The VH and VL gene identity (see I. M. Tomlinson, S. C. Williams, O. Ignatovitch, S. J. Corbett, and G. Winter, *V-BASE Sequence Directory*, Cambridge United Kingdom: MRC Centre for Protein Engineering (1997)) of one of the three scFvs specifically binding to H5, i.e., SC05-111, is depicted in Table 10.

From the selected specific single-chain phage antibody (scFv) clones specific for C-Ps, plasmid DNA was also obtained and nucleotide and amino acid sequences were determined according to standard techniques (data not shown). The sequences of the C-Ps-specific antibodies selected from both the IgM memory B cell library and IgM PBL library contained mutations in their VH gene with a high replacement to silent mutation ratio (see Table 11). This is an indication of an affinity maturation process and is a defining characteristic of antibodies derived from memory B cells. It also suggests that the VH genes from the positive-phage antibodies selected from the IgM PBL library came from memory IgM B cells. Thus, a library composed entirely of the rearranged V region gene pool present in IgM memory B cells produces more binding clones than an IgM PBL library and the produced binding clones are very likely of higher quality.

Example 5

Construction of Fully Human Immunoglobulin Molecules (Human Monoclonal Antibodies) from the Selected Single Chain Fvs Heavy- and light-chain variable regions of the H5-specific scFvs and heavy- and light-chain variable regions of four of the scFvs found by selecting the IgM memory library were cloned directly by restriction digest for expression in the IgG expression vectors pIg-C911-HCγ1, pIG-C909-Cκ or pIg-C910-Cλ. The resulting expression constructs encoding the human IgG1 heavy and light chains were transiently expressed in combination in 293T cells and supernatants containing human IgG1 antibodies were obtained and produced using standard purification procedures. The human IgG1 antibodies were validated for their ability to bind to H5 or C-Ps, as well as to a panel of diverse control antigens, influenza hemagglutinin H1 and H3 antigens, recombinant SARS spike fragment S318-510, rabies vaccine and West Nile virus-like particles. IgG1 molecules were incubated at 1 µg/ml with the panel of antigens. Additionally, a SARS-CoV-specific antibody, a rabies virus-specific antibody and a West Nile virus-specific antibody were included as control antibodies. The IgG1 molecules showed the same pattern of reactivity as demonstrated for the single-chain phage antibodies. The three anti-H5 antibodies bound specifically to H5, but not to any of the other control antigens (data not shown). Moreover, the four anti-C-Ps antibodies bound specifically to C-Ps, but not to any of the other control antigens (data not shown). To gauge the relative binding avidity, the specific anti-H5 antibodies were titrated in a concentration range of between 10 and 0.0003 µg/ml against H5 (see FIG. 1). As a negative control, an anti-West Nile virus antibody was used. From FIG. 1, it can be clearly deduced that one of the antibodies, CR5111, binds H5 with higher affinity than the other two, CR5108 and CR5109.

Figure 2:
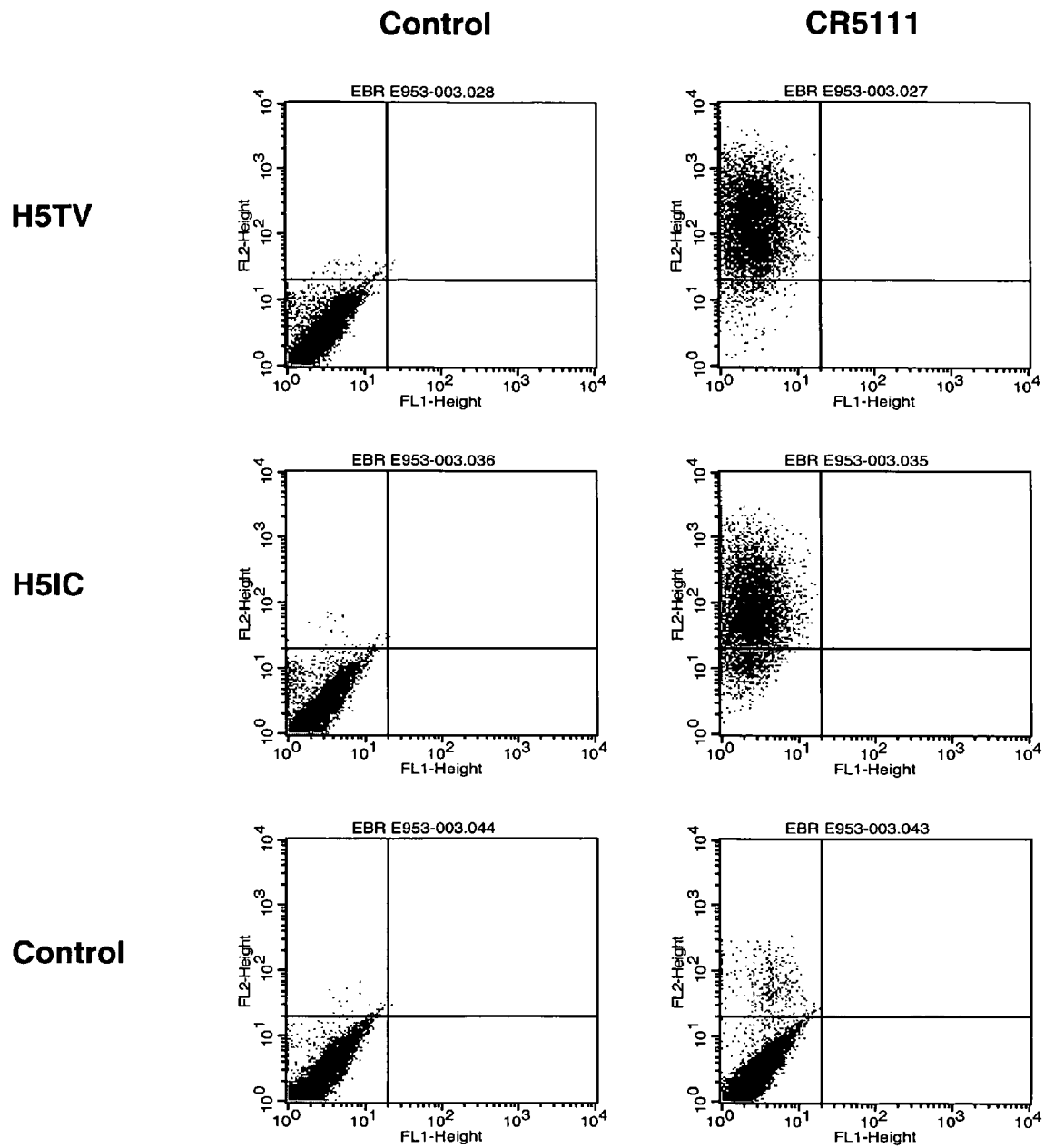

Subsequently, binding of IgG CR5111 to hemagglutinin-expressing PER.C6® cells was investigated by flow-cytometry. To this end, the complete coding sequence of HA from isolate A/Vietnam/1203/2004 (H5N1), representing the hemagglutinins identified in influenza strains isolated in Thailand and Vietnam (H5TV) in 2004 (clade 1) and a consensus sequence representing hemagglutinins of H5N1 strains isolated in Indonesia and China (H5IC) in 2003/2004 (clade 2) were cloned in expression vectors. H5TV and H5IC differ at nine amino acid positions, all located in the HA1 subunit of the molecule. The resulting H5-expression vectors and a control vector were used to transfect PER.C6® cells. FACS analysis for antibody binding to hemagglutinin demonstrated that antibody CR5111 bound to H5TV and H5IC-expressing PER.C6® cells (see FIG. 2). No significant binding of antibody CR5111 to control cells and binding of a control antibody to hemagglutinin-expressing cells was observed.

Figure 3:

To further investigate the specificity of antibody CR5111, an immunoblot analysis using SDS-PAGE separated proteins from hemagglutinin-expressing PER.C6® cells was performed. Polyclonal anti-H5 murine IgG recognized subunits HA1 and HA2, whereas antibody CR5111 solely recognized a linear epitope in the HA1 subunit (see FIG. 3). This is interesting, because the HA1 subunit is more variable than the HA2 subunit. Since binding of antibody CR5111 is obviously not affected by the amino acid differences between H5TV and H5IC, antibody CR5111 may bind to a variety of wild-type H5-hemagglutinins from the two clades. Its specificity makes it suitable for specifically targeting the HA1 subunit of H5N1.

Figure 4:
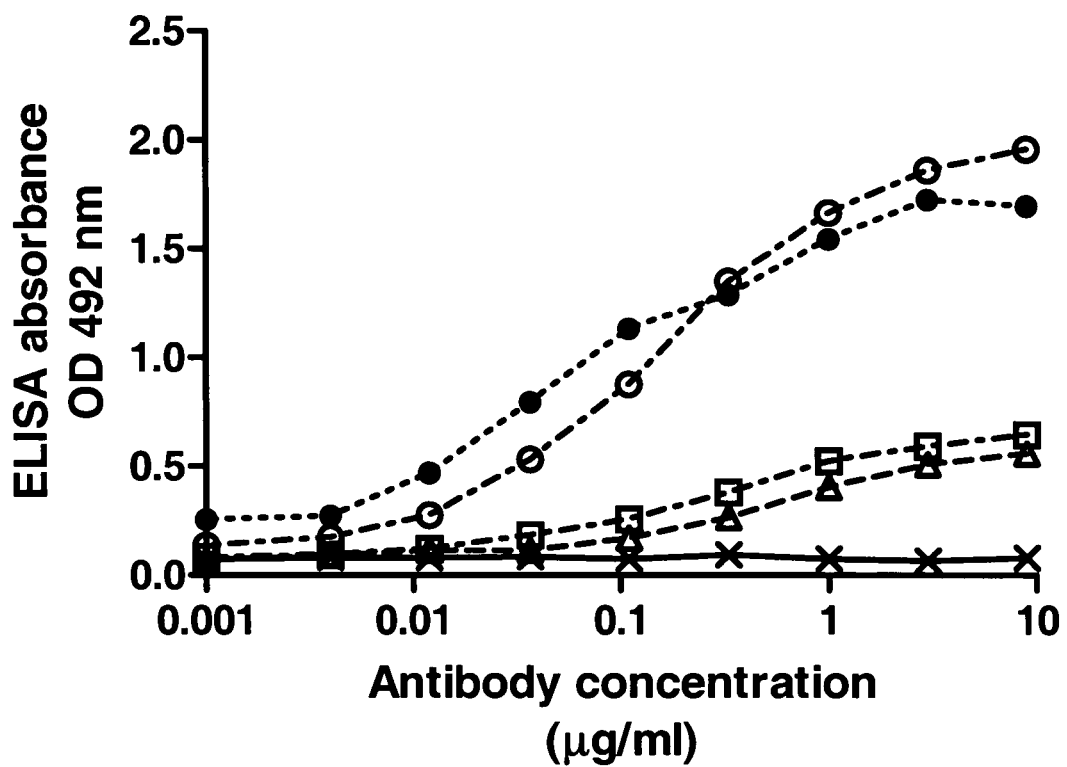

Furthermore, to gauge the relative binding avidity, the specific anti-C-Ps antibodies were titrated in a concentration range of between 10 and 0.0003 µg/ml against C-Ps (see FIG. 4). As a negative control, an anti-West Nile virus antibody was used. From FIG. 4, it can be clearly deduced that two of the antibodies bind C-Ps with higher affinity.

TABLE 1

First round Vκ, Vλ and VH amplifications

| Primer name | Primer nucleotide sequence | SEQ ID NO |
|---|---|---|
| OK1 (HUVK1B) | GAC ATC CAG WTG ACC CAG TCT CC | SEQ ID NO:1 |
| OK2 (HuVK2) | GAT GTT GTG ATG ACT CAG TCT CC | SEQ ID NO:2 |
| OK3 (HuVK2B2) | GAT ATT GTG ATG ACC CAG ACT CC | SEQ ID NO:3 |
| OK4 (HuVK3B) | GAA ATT GTG WTG ACR CAG TCT CC | SEQ ID NO:4 |
| OK5 (HuVK5) | GAA ACG ACA CTC ACG CAG TCT CC | SEQ ID NO:5 |
| OK6 (HuVK6) | GAA ATT GTG CTG ACT CAG TCT CC | SEQ ID NO:6 |
| OCK (HuCK) | ACA CTC TCC CCT GTT GAA GCT CTT | SEQ ID NO:7 |
| OL1 (HuVL1A)* | CAG TCT GTG CTG ACT CAG CCA CC | SEQ ID NO:8 |
| OL1 (HuVL1B)* | CAG TCT GTG YTG ACG CAG CCG CC | SEQ ID NO:9 |
| OL1 (HuVL1C)* | CAG TCT GTC GTG ACG CAG CCG CC | SEQ ID NO:10 |
| OL2 (HuVL2B) | CAG TCT GCC CTG ACT CAG CC | SEQ ID NO:11 |
| OL3 (HuVL3A) | TCC TAT GWG CTG ACT CAG CCA CC | SEQ ID NO:12 |
| OL4 (HuVL3B) | TCT TCT GAG CTG ACT CAG GAC CC | SEQ ID NO:13 |
| OL5 (HuVL4B) | CAG CYT GTG CTG ACT CAA TC | SEQ ID NO:14 |
| OL6 (HuVL5) | CAG GCT GTG CTG ACT CAG CCG TC | SEQ ID NO:15 |
| OL7 (HuVL6) | AAT TTT ATG CTG ACT CAG CCC CA | SEQ ID NO:16 |
| OL8 (HuVL7/8) | CAG RCT GTG GTG ACY CAG GAG CC | SEQ ID NO:17 |
| OL9 (HuVL9)# | CWG CCT GTG CTG ACT CAG CCM CC | SEQ ID NO:18 |
| OL9 (HuVL10)# | CAG GCA GGG CTG ACT CAG | SEQ ID NO:19 |
| OCL (HuCL2)X | TGA ACA TTC TGT AGG GGC CAC TG | SEQ ID NO:20 |
| OCL (HuCL7)X | AGA GCA TTC TGC AGG GGC CAC TG | SEQ ID NO:21 |
| OH1 (HuVH1B7A)+ | CAG RTG CAG CTG GTG CAR TCT GG | SEQ ID NO:22 |
| OH1 (HuVH1C)+ | SAG GTC CAG CTG GTR CAG TCT GG | SEQ ID NO:23 |
| OH2 (HuVH2B) | CAG RTG ACC TTG AAG GAG TCT GG | SEQ ID NO:24 |
| OH3 (HuVH3A) | GAG GTG CAG CTG GTG GAG | SEQ ID NO:25 |
| OH4 (HuVH3C) | GAG GTG CAG CTG GTG GAG WCY GG | SEQ ID NO:26 |
| OH5 (HuVH4B) | CAG GTG CAG CTA CAG CAG TGG GG | SEQ ID NO:27 |

TABLE 1-continued

First round Vκ, Vλ and VH amplifications

| Primer name | Primer nucleotide sequence | SEQ ID NO |
|---|---|---|
| OH6 (HuVH4C) | CAG STG CAG CTG CAG GAG TCS GG | SEQ ID NO:28 |
| OH7 (HuVH6A) | CAG GTA CAG CTG CAG CAG TCA GG | SEQ ID NO:29 |
| OCG (HuCIgG) | GTC CAC CTT GGT GTT GCT GGG CTT | SEQ ID NO:30 |
| OCM (HuCIgM) | TGG AAG AGG CAC GTT CTT TTC TTT | SEQ ID NO:31 |

*Mix in 1:1:1 ratio
Mix in 1:1 ratio
XMix in 1:1 ratio
+Mix in 1:1 ratio

TABLE 2

Second round Vκ, Vλ and VH amplifications

| Primer name | Primer nucleotide sequence | SEQ ID NO |
|---|---|---|
| OK1S (HuVK1B-SAL) | TGA GCA CAC AGG TCG ACG GAC ATC CAG WTG ACC CAG TCT CC | SEQ ID NO:32 |
| OK2S (HuVK2-SAL) | TGA GCA CAC AGG TCG ACG GAT GTT GTG ATG ACT CAG TCT CC | SEQ ID NO:33 |
| OK3S (HuVK2B2-SAL) | TGA GCA CAC AGG TCG ACG GAT ATT GTG ATG ACC CAG ACT CC | SEQ ID NO:34 |
| OK4S (HuVK3B-SAL) | TGA GCA CAC AGG TCG ACG GAA ATT GTG WTG ACR CAG TCT CC | SEQ ID NO:35 |
| OK5S (HuVK5-SAL) | TGA GCA CAC AGG TCG ACG GAA ACG ACA CTC ACG CAG TCT CC | SEQ ID NO:36 |
| OK6S (HuVK6-SAL) | TGA GCA CAC AGG TCG ACG GAA ATT GTG CTG ACT CAG TCT CC | SEQ ID NO:37 |
| OJK1 (HuJK1-NOT) | GAG TCA TTC TCG ACT TGC GGC CGC ACG TTT GAT TTC CAC CTT GGT CCC | SEQ ID NO:38 |
| OJK2 (HuJK2-NOT) | GAG TCA TTC TCG ACT TGC GGC CGC ACG TTT GAT CTC CAG CTT GGT CCC | SEQ ID NO:39 |
| OJK3 (HuJK3-NOT) | GAG TCA TTC TCG ACT TGC GGC CGC ACG TTT GAT ATC CAC TTT GGT CCC | SEQ ID NO:40 |
| OJK4 (HuJK4-NOT) | GAG TCA TTC TCG ACT TGC GGC CGC ACG TTT GAT CTC CAC CTT GGT CCC | SEQ ID NO:41 |
| OJK5 (HuJK5-NOT) | GAG TCA TTC TCG ACT TGC GGC CGC ACG TTT AAT CTC CAG TCG TGT CCC | SEQ ID NO:42 |
| OL1S (HuVL1A-SAL)* | TGA GCA CAC AGG TCG ACG CAG TCT GTG CTG ACT CAG CCA CC | SEQ ID NO:43 |
| OL1S (HuVL1B-SAL)* | TGA GCA CAC AGG TCG ACG CAG TCT GTG YTG ACG CAG CCG CC | SEQ ID NO:44 |
| OL1S (HuVL1C-SAL)* | TGA GCA CAC AGG TCG ACG CAG TCT GTC GTG ACG CAG CCG CC | SEQ ID NO:45 |
| OL2S (HuVL2B-SAL) | TGA GCA CAC AGG TCG ACG CAG TCT GCC CTG ACT CAG CC | SEQ ID NO:46 |
| OL3S (HuVL3A-SAL) | TGA GCA CAC AGG TCG ACG TCC TAT GWG CTG ACT CAG CCA CC | SEQ ID NO:47 |
| OL4S (HuVL3B-SAL) | TGA GCA CAC AGG TCG ACG TCT TCT GAG CTG ACT CAG GAC CC | SEQ ID NO:48 |

TABLE 2-continued

Second round Vκ, Vλ and VH amplifications

| Primer name | Primer nucleotide sequence | SEQ ID NO |
|---|---|---|
| OL5S (HuVL4B-SAL) | TGA GCA CAC AGG TCG ACG CAG CYT GTG CTG ACT CAA TC | SEQ ID NO:49 |
| OL6S (HuVL5-SAL) | TGA GCA CAC AGG TCG ACG CAG GCT GTG CTG ACT CAG CCG TC | SEQ ID NO:50 |
| OL7S (HuVL6-SAL) | TGA GCA CAC AGG TCG ACG AAT TTT ATG CTG ACT CAG CCC CA | SEQ ID NO:51 |
| OL8S (HuVL7/8-SAL) | TGA GCA CAC AGG TCG ACG CAG RCT GTG GTG ACY CAG GAG CC | SEQ ID NO:52 |
| OL9S (HuVL9-SAL)# | TGA GCA CAC AGG TCG ACG CWG CCT GTG CTG ACT CAG CCM CC | SEQ ID NO:53 |
| OL9S (HuVL10-SAL)# | TGA GCA CAC AGG TCG ACG CAG GCA GGG CTG ACT CAG | SEQ ID NO:54 |
| OJL1 (HuJL1-NOT) | GAG TCA TTC TCG ACT TGC GGC CGC ACC TAG GAC GGT GAC CTT GGT CCC | SEQ ID NO:55 |
| OJL2 (HuJL2/3-NOT) | GAG TCA TTC TCG ACT TGC GGC CGC ACC TAG GAC GGT CAG CTT GGT CCC | SEQ ID NO:56 |
| OJL3 (HuJL7-NOT) | GAG TCA TTC TCG ACT TGC GGC CGC ACC GAG GAC GGT CAG CTG GGT GCC | SEQ ID NO:57 |
| OH1S (HuVH1B-SFI)+ | GTC CTC GCA ACT GCG GCC CAG CCG GCC ATG GCC CAG RTG CAG CTG GTG CAR TCT GG | SEQ ID NO:58 |
| OH1S (HuVH1C-SFI)+ | GTC CTC GCA ACT GCG GCC CAG CCG GCC ATG GCC SAG GTC CAG CTG GTR CAG TCT GG | SEQ ID NO:59 |
| OH2S (HuVH2B-SFI) | GTC CTC GCA ACT GCG GCC CAG CCG GCC ATG GCC CAG RTC ACC TTG AAG GAG TCT GG | SEQ ID NO:60 |
| OH3S (HuVH3A-SFI) | GTC CTC GCA ACT GCG GCC CAG CCG GCC ATG GCC GAG GTG CAG CTG GTG GAG | SEQ ID NO:61 |
| OH4S (HuVH3C-SFI) | GTC CTC GCA ACT GCG GCC CAG CCG GCC ATG GCC GAG GTG CAG CTG GTG GAG WCY GG | SEQ ID NO:62 |
| OH5S (HuVH4B-SFI) | GTC CTC GCA ACT GCG GCC CAG CCG GCC ATG GCC CAG GTG CAG CTA CAG CAG TGG GG | SEQ ID NO:63 |
| OH6S (HuVH4C-SFI) | GTC CTC GCA ACT GCG GCC CAG CCG GCC ATG GCC CAG STG CAG CTG CAG GAG TCS GG | SEQ ID NO:64 |
| OH7S (HuVH6A-SFI) | GTC CTC GCA ACT GCG GCC CAG CCG GCC ATG GCC CAG GTA CAG CTG CAG CAG TCA GG | SEQ ID NO:65 |
| OJH1 (HuJH1/2-XHO) | GAG TCA TTC TCG ACT CGA GAC RGT GAC CAG GGT GCC | SEQ ID NO:66 |
| OJH2 (HuJH3-XHO) | GAG TCA TTC TCG ACT CGA GAC GGT GAC CAT TGT CCC | SEQ ID NO:67 |

TABLE 2-continued

Second round Vκ, Vλ and VH amplifications

| Primer name | Primer nucleotide sequence | SEQ ID NO |
|---|---|---|
| OJH3 (HuJH4/5-XHO) | GAG TCA TTC TCG ACT CGA GAC GGT GAC CAG GGT TCC | SEQ ID NO:68 |
| OJH4 (HuJH6-XHO) | GAG TCA TTC TCG ACT CGA GAC GGT GAC CGT GGT CCC | SEQ ID NO:69 |

*Mix in 1:1:1 ratio
Mix in 1:1 ratio
†Mix in 1:1 ratio

TABLE 3

Second round $V_L$ regions amplification overview

| Template | 5' primer | 3' primer | Product | Share in PK/PL (%) | Pool | Share in $V_L$ (%) |
|---|---|---|---|---|---|---|
| K1 | OK1S | OJK1 | K1J1 | 25 | PK1 | 30 |
|    | OK1S | OJK2 | K1J2 | 25 |     |    |
|    | OK1S | OJK3 | K1J3 | 10 |     |    |
|    | OK1S | OJK4 | K1J4 | 25 |     |    |
|    | OK1S | OJK5 | K1J5 | 15 |     |    |
| K2 | OK2S | OJK1 | K2J1 | 25 | PK2 | 4  |
|    | OK2S | OJK2 | K2J2 | 25 |     |    |
|    | OK2S | OJK3 | K2J3 | 10 |     |    |
|    | OK2S | OJK4 | K2J4 | 25 |     |    |
|    | OK2S | OJK5 | K2J5 | 15 |     |    |
| K3 | OK3S | OJK1 | K3J1 | 25 | PK3 | 1  |
|    | OK3S | OJK2 | K3J2 | 25 |     |    |
|    | OK3S | OJK3 | K3J3 | 10 |     |    |
|    | OK3S | OJK4 | K3J4 | 25 |     |    |
|    | OK3S | OJK5 | K3J5 | 15 |     |    |
| K4 | OK4S | OJK1 | K4J1 | 25 | PK4 | 19 |
|    | OK4S | OJK2 | K4J2 | 25 |     |    |
|    | OK4S | OJK3 | K4J3 | 10 |     |    |
|    | OK4S | OJK4 | K4J4 | 25 |     |    |
|    | OK4S | OJK5 | K4J5 | 15 |     |    |
| K5 | OK5S | OJK1 | K5J1 | 25 | PK5 | 1  |
|    | OK5S | OJK2 | K5J2 | 25 |     |    |
|    | OK5S | OJK3 | K5J3 | 10 |     |    |
|    | OK5S | OJK4 | K5J4 | 25 |     |    |
|    | OK5S | OJK5 | K5J5 | 15 |     |    |
| K6 | OK6S | OJK1 | K6J1 | 25 | PK6 | 5  |
|    | OK6S | OJK2 | K6J2 | 25 |     |    |
|    | OK6S | OJK3 | K6J3 | 10 |     |    |
|    | OK6S | OJK4 | K6J4 | 25 |     |    |
|    | OK6S | OJK5 | K6J5 | 15 |     |    |
| L1 | OL1S | OJL1 | L1J1 | 30 | PL1 | 14 |
|    | OL1S | OJL2 | L1J2 | 60 |     |    |
|    | OL1S | OJL3 | L1J3 | 10 |     |    |
| L2 | OL2S | OJL1 | L2J1 | 30 | PL2 | 10 |
|    | OL2S | OJL2 | L2J2 | 60 |     |    |
|    | OL2S | OJL3 | L2J3 | 10 |     |    |
| L3 | OL3S | OJL1 | L3J1 | 30 | PL3 | 10 |
|    | OL3S | OJL2 | L3J2 | 60 |     |    |
|    | OL3S | OJL3 | L3J3 | 10 |     |    |
| L4 | OL4S | OJL1 | L4J1 | 30 | PL4 | 1  |
|    | OL4S | OJL2 | L4J2 | 60 |     |    |
|    | OL4S | OJL3 | L4J3 | 10 |     |    |
| L5 | OL5S | OJL1 | L5J1 | 30 | PL5 | 1  |
|    | OL5S | OJL2 | L5J2 | 60 |     |    |
|    | OL5S | OJL3 | L5J3 | 10 |     |    |
| L6 | OL6S | OJL1 | L6J1 | 30 | PL6 | 1  |
|    | OL6S | OJL2 | L6J2 | 60 |     |    |
|    | OL6S | OJL3 | L6J3 | 10 |     |    |
| L7 | OL7S | OJL1 | L7J1 | 30 | PL7 | 1  |
|    | OL7S | OJL2 | L7J2 | 60 |     |    |
|    | OL7S | OJL3 | L7J3 | 10 |     |    |
| L8 | OL8S | OJL1 | L8J1 | 30 | PL8 | 1  |
|    | OL8S | OJL2 | L8J2 | 60 |     |    |
|    | OL8S | OJL3 | L8J3 | 10 |     |    |
| L9 | OL9S | OJL1 | L9J1 | 30 | PL9 | 1  |
|    | OL9S | OJL2 | L9J2 | 60 |     |    |
|    | OL9S | OJL3 | L9J3 | 10 |     |    |
|    |      |      |      |    | $V_L$ | 100% |

TABLE 4

Second round $V_L$ regions amplification overview

| Template | 5' primer | 3' primer | Product | Share in PK/PL (%) | Pool | Share in $V_L$ (%) |
|---|---|---|---|---|---|---|
| H1 | OH1S | OJH1 | H1J1 | 10 | PH1 | 25 |
|    | OH1S | OJH2 | H1J2 | 10 |     |    |
|    | OH1S | OJH3 | H1J3 | 60 |     |    |
|    | OH1S | OJH4 | H1J4 | 20 |     |    |
| H2 | OH2S | OJH1 | H2J1 | 10 | PH2 | 2  |
|    | OH2S | OJH2 | H2J2 | 10 |     |    |
|    | OH2S | OJH3 | H2J3 | 60 |     |    |
|    | OH2S | OJH4 | H2J4 | 20 |     |    |
| H3 | OH3S | OJH1 | H3J1 | 10 | PH3 | 25 |
|    | OH3S | OJH2 | H3J2 | 10 |     |    |
|    | OH3S | OJH3 | H3J3 | 60 |     |    |
|    | OH3S | OJH4 | H3J4 | 20 |     |    |
| H4 | OH4S | OJH1 | H4J1 | 10 | PH4 | 25 |
|    | OH4S | OJH2 | H4J2 | 10 |     |    |
|    | OH4S | OJH3 | H4J3 | 60 |     |    |
|    | OH4S | OJH4 | H4J4 | 20 |     |    |
| H5 | OH5S | OJH1 | H5J1 | 10 | PH5 | 2  |
|    | OH5S | OJH2 | H5J2 | 10 |     |    |
|    | OH5S | OJH3 | H5J3 | 60 |     |    |
|    | OH5S | OJH4 | H5J4 | 20 |     |    |
| H6 | OH6S | OJH1 | H6J1 | 10 | PH6 | 20 |
|    | OH6S | OJH2 | H6J2 | 10 |     |    |
|    | OH6S | OJH3 | H6J3 | 60 |     |    |
|    | OH6S | OJH4 | H6J4 | 20 |     |    |

TABLE 4-continued

Second round $V_L$ regions amplification overview

| Template | 5' primer | 3' primer | Product | Share in PK/PL (%) | Pool | Share in $V_L$ (%) |
|---|---|---|---|---|---|---|
| H7 | OH7S | OJH1 | H7J1 | 10 | PH7 | 1 |
| | OH7S | OJH2 | H7J2 | 10 | | |
| | OH7S | OJH3 | H7J3 | 60 | | |
| | OH7S | OJH4 | H7J4 | 20 | | |
| | | | | | $V_H$ | 100% |

TABLE 5

Characteristics of the individual IgM memory B cell libraries.
IgM memory libraries

| | Cells | | Libraries | | | |
|---|---|---|---|---|---|---|
| Donor | Total PBL (×10⁶) | % memory B cells | Size (×10⁶) | % Insert frequency | % ORF | % Unique |
| Individual 1 | | | 3 | 96 | 74 | 98 |
| Individual 2 | 72.5 | 1.7 | 5 | 98 | 79 | 98 |
| Individual 3 | 67.5 | 1.4 | 3 | 96 | 79 | 98 |
| Individual 4 | 132.5 | 2.3 | 6 | 98 | 69 | 99 |

TABLE 6

Binding of single-chain (scFv) phage antibodies selected from IgM memory B cell libraries to H5, Protifar milk powder and BSA as measured by ELISA at 492 nm.

| Antibody name | H5 | Protifar | BSA |
|---|---|---|---|
| SC05-104 | 1.303 | 1.35 | 0.091 |
| SC05-105 | 0.057 | 1.463 | 0.041 |
| SC05-106 | 0.047 | 1.168 | 0.047 |
| SC05-107 | 1.144 | 1.287 | 0.107 |
| SC05-108 | 0.524 | 0.047 | 0.043 |
| SC05-109 | 0.303 | 0.046 | 0.039 |
| SC05-110 | 0.43 | 1.576 | 0.213 |
| SC05-111 | 1.216 | 0.053 | 0.051 |
| SC05-112 | 0.049 | 1.627 | 0.038 |
| SC05-113 | 0.057 | 1.59 | 0.045 |
| Control | 0.048 | 0.048 | 0.043 |

TABLE 7

Amino acid mutations and replacement to silent ratio in the VH gene of H5 selected antibodies.

| Library | Antibody name | # AA mutations | R/S ratio |
|---|---|---|---|
| IgM memory | SC05-104 | 7 | 0.571 |
| IgM memory | SC05-105 | 4 | 0.75 |
| IgM memory | SC05-106 | 2 | 0.5 |
| IgM memory | SC05-107 | 5 | 0.8 |
| IgM memory | SC05-108 | 5 | 0.6 |
| IgM memory | SC05-109 | 0 | 0 |
| IgM memory | SC05-110 | 7 | 0.857 |
| IgM memory | SC05-111 | 11 | 0.636 |
| IgM memory | SC05-112 | 9 | 0.667 |
| IgM memory | SC05-113 | 7 | 0.714 |

TABLE 8

Binding of single-chain (scFv) phage antibodies selected from IgM memory B cell libraries to C-ps, Protifar milk powder and BSA as measured by ELISA at 492 nm.

| Antibody name | C-ps | Protifar | BSA |
|---|---|---|---|
| SC05-094 | 0.283 | 0.054 | 0.056 |
| SC05-095 | 1.340 | 0.041 | 0.040 |
| SC05-096 | 0.048 | 1.411 | 0.042 |
| SC05-097 | 0.701 | 0.036 | 0.039 |
| SC05-098 | 1.011 | 0.037 | 0.041 |
| SC05-100 | 1.363 | 0.051 | 0.046 |
| SC05-101 | 0.867 | 1.286 | 0.077 |
| SC05-102 | 0.989 | 0.509 | 0.055 |
| SC05-114 | 1.368 | 0.049 | 0.040 |
| Control | 0.049 | 0.047 | 0.051 |

TABLE 9

Binding of single-chain (scFv) phage antibodies selected from IgM PBL libraries to C-ps, Protifar milk powder and BSA as measured by ELISA at 492 nm.

| Antibody name | C-ps | Protifar | BSA |
|---|---|---|---|
| SC05-119 | 0.539 | 0.049 | ND |
| SC05-120 | 0.586 | 0.061 | ND |
| Control | 0.047 | 0.047 | ND |

TABLE 10

Data of single-chain Fv capable of binding H5.

| Name scFv | HCDR3 | VH-germline | VL-germline |
|---|---|---|---|
| SC05-111 | GRGYCSGGVCYVDY (SEQ ID NO:74) | 3-21 (DP-77) | Vk III (L6) |

TABLE 11

Amino acid mutations and replacement to silent ratio in the VH gene of C-Ps selected antibodies.

| Library | Antibody name | # AA mutations | R/S ratio |
|---|---|---|---|
| IgM memory | SC05-094 | 7 | 0.88 |
| IgM memory | SC05-095 | 1 | 1 |
| IgM memory | SC05-096 | 6 | 0.67 |
| IgM memory | SC05-097 | 5 | 0.56 |
| IgM memory | SC05-098 | 9 | 0.75 |
| IgM memory | SC05-100 | 2 | 1 |
| IgM memory | SC05-101 | 3 | 1 |
| IgM memory | SC05-102 | 2 | 1 |
| IgM memory | SC05-114 | 3 | 0.60 |
| IgM PBL | SC05-119 | 13 | 0.68 |
| IgM PBL | SC05-120 | 8 | 0.72 |

REFERENCES

Boel E., S. Verlaan, M. J. Poppelier, N. A. Westerdaal, J. A. Van Strijp and T. Logtenberg (2000). Functional human monoclonal antibodies of all isotypes constructed from phage display library-derived single-chain Fv antibody fragments. *J. Immunol. Methods* 239:153-166.

Burton D. R. and C. F. Barbas (1994). Human antibodies from combinatorial libraries. *Adv. Immunol.* 57:191-280.

Dancer S. J. (2004). How antibiotics can make us sick: the less obvious adverse effects of antimicrobial chemotherapy. *Lancet Infect. Dis.* 4:611-619.

De Kruif J., E. Boel and T. Logtenberg (1995). Selection and application of human single-chain Fv antibody fragments from a semi-synthetic phage antibody display library with designed CDR3 regions. *J. Mol. Biol.* 248:97-105.

Germain R. N. (2004). An innately interesting decade of research in immunology. *Nat. Med.* 10:1307-1320.

Huls G., I. J. Heijnen, E. Cuomo, J. van der Linden, E. Boel, J. van de Winkel and T. Logtenberg (1999). Antitumor immune effector mechanisms recruited by phage display-derived fully human IgG1 and IgA1 monoclonal antibodies. *Cancer Res.* 59:5778-5784.

Musher D. M., M. J. Luchi, D. A. Watson, R. Hamilton and R. E. Baughn (1990). Pneumococcal polysaccharide vaccine in young adults and older bronchitics: determination of IgG responses by ELISA and the effect of adsorption of serum with non-type-specific cell wall polysaccharide. *J. Infect. Dis.* 161:728-735.

Spellberg B., J. H. Powers, E. P. Brass, L. G. Miller and J. E. Edwards, Jr. (2004). Trends in antimicrobial drug development: implications for the future. *Clin. Infect. Dis.* 38:1279-1286.

Wisplinghoff H., T. Bischoff, S. M. Tallent, H. Seifert, R. P. Wenzel and M. B. Edmond (2004). Nosocomial bloodstream infections in U.S. hospitals: analysis of 24,179 cases from a prospective nationwide surveillance study. *Clin. Infect. Dis.* 39:309-317.

---

The invention claimed is:

1. A method for generating an immunoglobulin library comprising:
   isolating RNA from a subset of B cells consisting essentially of CD24+/CD27+/IgM+ cells, and
   preparing an immunoglobulin library from the isolated RNA.

2. The method according to claim 1, further comprising deriving the subset of B cells from a single individual before isolating the subset of B cells.

3. The method according to claim 1, further comprising displaying immunoglobulins of the subset of B cells on the surface of replicable genetic packages.

4. The method according to claim 1, wherein the prepared immunoglobulin library is selected from the group consisting of an antibody library, a single chain Fv library and a Fab library.

5. A method for generating an immunoglobulin library, wherein the method comprises the steps of:
   a) isolating a subset of B cells from an individual, wherein the subset of B cells consists essentially of CD24+/CD27+/IgM+ cells,
   b) isolating RNA from the subset of B cells, c) converting the isolated RNA into cDNA,
   d) amplifying immunoglobulin nucleic acid molecules of said cDNA,
   e) inserting the amplified immunoglobulin nucleic acid molecules into at least one vector, and
   f) transforming at least one host cell with the at least one vector containing the amplified nucleic acid molecules to obtain an immunoglobulin library.

6. The method according to claim 1, further comprising:
   screening the prepared immunoglobulin library for an immunoglobulin having a functionality of interest.

7. The method according to claim 6, wherein screening the prepared immunoglobulin library for an immunoglobulin having a functionality of interest comprises:

a) contacting the prepared immunoglobulin library with an antigen under conditions conducive to binding,
   b) separating and recovering immunoglobulins that bind to the antigen from immunoglobulins that do not bind,
   c) isolating at least one recovered immunoglobulin,
   d) screening if the immunoglobulin isolated has a functionality of interest, and
   e) isolating an immunoglobulin having the functionality of interest.

8. The method according to claim 3, wherein the replicable genetic package is selected from the group consisting of a phage particle, a bacterium, a yeast, a fungus, a spore of a microorganism, and a ribosome.

9. The method according to claim 8, wherein the immunoglobulin library is selected from the group consisting of an antibody library, a single chain Fv library, and a Fab library.

10. The method according to claim 2, further comprising displaying immunoglobulins of the subset of B cells on the surface of a replicable genetic package, wherein the replicable genetic package is selected from the group consisting of a phage particle, a bacterium, a yeast, a fungus, a spore of a microorganism, and a ribosome.

11. The method according to claim 10, wherein the immunoglobulin library is selected from the group consisting of an antibody library, a single chain Fv library, and a Fab library.

12. The method according to claim 2, wherein the single individual is a human.

13. The method according to claim 12, further comprising displaying immunoglobulins of the subset of B cells on the surface of a replicable genetic package, wherein the replicable genetic package is selected from the group consisting of a phage particle, a bacterium, a yeast, a fungus, a spore of a microorganism, and a ribosome.

14. The method according to claim 13, wherein the immunoglobulin library is selected from the group consisting of an antibody library, a single chain Fv library, and a Fab library.

15. The method according to claim 1 wherein at least 90% of the cells used to prepare the library are CD24+/CD27+/IgM+ B cells.

16. The method according to claim 1 wherein at least 92% of the cells used to prepare the library are CD24+/CD27+/IgM+ B cells.

17. The method according to claim 1 wherein at least 95% of the cells used to prepare the library are CD24+/CD27+/IgM+ B cells.

18. The method according to claim 1 wherein at least 97% of the cells used to prepare the library are CD24+/CD27+/IgM+ B cells.

19. The method according to claim 5, wherein at least 90% of the cells used to prepare the library are CD24+/CD27+/IgM+ B cells.

20. The method according to claim 5, wherein at least 92% of the cells used to prepare the library are CD24+/CD27+/IgM+ B cells.

21. The method according to claim 5, wherein at least 95% of the cells used to prepare the library are CD24+/CD27+/IgM+ B cells.

22. The method according to claim 5, wherein at least 97% of the cells used to prepare the library are CD24+/CD27+/IgM+ B cells.

* * * * *

UNITED STATES PATENT AND TRADEMARK OFFICE
CERTIFICATE OF CORRECTION

PATENT NO. : 8,642,513 B2  Page 1 of 1
APPLICATION NO. : 11/990974
DATED : February 4, 2014
INVENTOR(S) : Throsby et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 923 days.

Signed and Sealed this

Twenty-ninth Day of September, 2015

Michelle K. Lee
*Director of the United States Patent and Trademark Office*